(12) United States Patent
Vaddi et al.

(10) Patent No.: US 10,272,045 B2
(45) Date of Patent: Apr. 30, 2019

(54) HIGH SURFACE-AREA LYOPHILIZED COMPOSITIONS COMPRISING ARSENIC FOR ORAL ADMINISTRATION IN PATIENTS

(71) Applicant: Orsenix Holdings BV, Wilmington, DE (US)

(72) Inventors: Krishna Vaddi, Kennett Square, PA (US); Kumar Kurumaddali, New York, NY (US)

(73) Assignee: Orsenix Holdings BV, Wilmington, DE (US)

( * ) Notice: Subject to any disclaimer, the term of this patent is extended or adjusted under 35 U.S.C. 154(b) by 0 days.

(21) Appl. No.: 16/148,193

(22) Filed: Oct. 1, 2018

(65) Prior Publication Data

US 2019/0029963 A1 Jan. 31, 2019

Related U.S. Application Data

(62) Division of application No. 15/012,355, filed on Feb. 1, 2016, now Pat. No. 10,111,836.

(60) Provisional application No. 62/142,709, filed on Apr. 3, 2015, provisional application No. 62/110,574, filed on Feb. 1, 2015.

(51) Int. Cl.
| | | |
|---|---|---|
| *A61K 33/36* | (2006.01) | |
| *A61K 31/285* | (2006.01) | |
| *A23C 1/06* | (2006.01) | |
| *A61K 9/19* | (2006.01) | |
| *A61K 47/10* | (2017.01) | |
| *A61K 9/48* | (2006.01) | |
| *A61K 47/20* | (2006.01) | |
| *A61K 47/02* | (2006.01) | |
| *A61K 47/26* | (2006.01) | |
| *A61K 45/06* | (2006.01) | |

(52) U.S. Cl.
CPC ............... *A61K 9/19* (2013.01); *A61K 9/48* (2013.01); *A61K 9/4858* (2013.01); *A61K 33/36* (2013.01); *A61K 45/06* (2013.01); *A61K 47/02* (2013.01); *A61K 47/10* (2013.01); *A61K 47/20* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 6,723,351 B2 | 4/2004 | Warrell, Jr. | |
| 6,770,304 B2 | 8/2004 | Warrell, Jr. | |
| 6,855,339 B2 | 2/2005 | Warrell, Jr. | |
| 6,861,076 B2 | 3/2005 | Warrell, Jr. | |
| 6,884,439 B2 | 4/2005 | Warrell, Jr. | |
| 6,982,096 B2 | 1/2006 | Warrell, Jr. | |
| 7,276,359 B1 | 10/2007 | Musunuri et al. | |
| 7,521,071 B2 | 4/2009 | Kumana | |
| 7,879,364 B2 | 2/2011 | Warrell, Jr. | |
| 8,273,379 B2 | 9/2012 | Warrell, Jr. | |
| 8,906,422 B2 | 12/2014 | Kwong | |
| 2002/0013371 A1 | 1/2002 | Warrell, Jr. | |
| 2003/0077297 A1 | 4/2003 | Chen et al. | |
| 2003/0099719 A1 | 5/2003 | Warrell | |
| 2004/0101573 A1 | 5/2004 | Zhang | |
| 2004/0126434 A1 | 7/2004 | Kumana et al. | |
| 2005/0101524 A1 | 5/2005 | Hogg | |
| 2006/0120973 A1 | 6/2006 | Dyer | |
| 2009/0162440 A1 | 6/2009 | Xiaoping et al. | |
| 2010/0166872 A1 | 7/2010 | Singh et al. | |
| 2012/0245156 A1 | 9/2012 | Nguyen | |
| 2014/0370119 A1 | 12/2014 | Lou et al. | |

FOREIGN PATENT DOCUMENTS

| | | |
|---|---|---|
| CN | 1546058 | 11/2004 |
| CN | 1698650 | 11/2005 |
| CN | 1326528 | 7/2007 |

(Continued)

OTHER PUBLICATIONS

PubChem CID entry 5281955 for Polysorbate 80; pdf download; Dec. 3, 2018.*
Song et al., "Preparation and Investigation of Arsenic Trioxide-loaded Polylactic Acid/Magnetic Hybrid nanoparticles", Chemical Research in Chinese Universities and Springer-Verlag GmbH, 30(2), pp. 326-332, 2014.
Handbook of Pharmaceutical Excipients; Oct. 13, 1988; entry for Mannitol (5-pg pdf); HoPE pp. 177-180.
Kwong, et al., Delicious poison: arsenic trioxide for the treatment of leukemia, Blood, 1997; 89:3487-8.
Chen et al., Use of arsenic trioxide ($As_2O_3$) in the treatment of acute promyelocytic leukemia (APL): I. $As_2O_3$ exerts dose-dependent dual effect on APL cells in vitro and in vivo, Blood, 1997; 89: 3345-53.

(Continued)

*Primary Examiner* — Jeffrey T. Palenik
(74) *Attorney, Agent, or Firm* — BakerHostetler

(57) ABSTRACT

The present invention relates to treating malignancies such as tumors or cancers by orally administering lyophilized compositions comprising arsenic to a subject in such need. Malignancies include various hematological malignancies, such as acute myeloid leukemia (AML) including acute promyelocytic leukemia (APL), myelodysplastic syndrome (MDS), multiple myeloma (MM) and lymphomas and solid tumors including glioblastoma multiforme and breast cancer. Arsenic treatment has shown great promise in the treatment of several cancers but requires daily intravenous (IV) administration. This invention relates to a novel formulation comprising a lyophilized compositions comprising arsenic. As a result, the formulation facilitates a systemic bioavailability comparable to that of intravenous (IV) administration of arsenic trioxide currently practiced. The present invention also relates to a method for lyophilizing the arsenic trioxide, preparing the oral formulation comprising lyophilized compositions comprising arsenic, and a method for treating a subject with malignancies using the oral formulation.

26 Claims, 9 Drawing Sheets

(56) References Cited

FOREIGN PATENT DOCUMENTS

| CN | 101322719 | | 3/2012 |
|---|---|---|---|
| CN | 103142648 | A | 6/2013 |
| CN | 103340899 | A | 10/2013 |
| CN | 103408477 | | 11/2013 |

OTHER PUBLICATIONS

Soignet et al., United States multicenter study of arsenic trioxide in relapsed acute promyelocytic leukemia, J. Clin. Oncol., 2001;19:3852-60.

Shen et al., Use of arsenic trioxide ($As_2O_3$) in the treatment of acute promyelocytic leukemia (APL): II. Clinical efficacy and pharmacokinetics in relapsed patients, Blood 1997; 89:3354-60.

Soignet et al., Complete remission after treatment of acute promyelocytic leukemia with arsenic trioxide, N Engl J Med 1998;339:1341-8.

Niu et al., Studies on treatment of acute promyelocytic leukemia with arsenic trioxide: remission induction, follow-up and molecular monitoring in 11 newly diagnosed and 47 relapsed acute promyelocytic leukemia patients, Blood 1999;94:3315-24.

\* cited by examiner 5.0 PROCESS FLOW DIAGRAM:

HIGH SURFACE-AREA LYOPHILIZED COMPOSITIONS COMPRISING ARSENIC FOR ORAL ADMINISTRATION IN PATIENTS

CROSS REFERENCE TO RELATED APPLICATIONS

This Application is a divisional application of co-pending U.S. application Ser. No. 15/012,355, filed on Feb. 1, 2016, which claims the benefit of U.S. Provisional Application No. 62/110,574, filed Feb. 1, 2015, and U.S. Provisional Application No. 62/142,709, filed Apr. 3, 2015, each of which is incorporated by reference herein in their entirety.

TECHNICAL FIELD

The present invention relates to treating malignancies such as tumors or cancers by administering lyophilized compositions comprising arsenic to a subject. Malignancies include various hematological malignancies, such as acute myeloid leukemia (AML) including acute promyelocytic leukemia (APL), myelodysplastic syndrome (MDS), multiple myeloma (MM), and lymphomas; and solid tumors including glioblastoma multiforme, and breast cancer.

Conventional arsenic treatment has shown great promise in the treatment of several cancers, but requires daily intravenous (IV) administration. In contrast, the oral formulation of the present invention provides a systemic bioavailability comparable to that of intravenous (IV) administration of arsenic trioxide that is being currently practiced. It also exhibits the shelf life of more than three (3) months and provides a much more convenient, less risky, and less expensive method of administering arsenic trioxide than that provided by the intravenous administration methods. The present invention also relates to method for preparing the lyophilized composition comprising arsenic, method for preparing the oral formulation of the present invention, method for orally administering the formulation to a subject, and a method for treating a subject with malignancies, for example, hematological malignancies, using the oral formulation.

BACKGROUND

Hematological Malignancies

Hematological malignancies are cancers of the body's blood-forming systems and immune systems. Hematological malignancies include, for example, leukemia, lymphoma (both Hodgkin's disease and non-Hodgkin's lymphoma), and myeloma. The abnormal cell growth interferes with the body's production of healthy blood cells, thus making the body unable to protect itself against infections.

New cases of hematological malignancies account for about 9 percent of cancer cases diagnosed in the United States, and about 59,200 persons are killed by the diseases each year. Many of these diseases occur in children.

Leukemia

Leukemia is a cancer of the bone marrow and blood. It is characterized by the uncontrolled growth of blood cells. About 30,000 new cases of leukemia are reported in the United States each year. Most cases occur in older adults, though leukemia is the most common type of childhood cancer.

Leukemia is either acute or chronic. In acute leukemia, the abnormal blood cells are blasts that remain very immature and cannot carry out their normal functions. The number of blasts increases rapidly, and the disease worsens rapidly. In chronic leukemia, some blast cells are present, but in general, these cells are more mature and can carry out some of their normal functions. Also, the number of blasts increases less rapidly than in acute leukemia. As a result, chronic leukemia worsens gradually.

Leukemia can arise in either of the two main types of white blood cells—lymphoid cells (lymphocytic leukemia) or myeloid cells (myeloid or myelogenous leukemia). Common types of leukemia include acute lymphocytic leukemia (ALL); acute myeloid leukemia (AML) (sometimes called acute nonlymphocytic leukemia (ANLL)) such as myeloblastic, promyelocytic, myelomonocytic, monocytic, erythroleukemia leukemias acute neutrophilic leukemia and myelodysplastic syndrome (MDS); chronic lymphocytic leukemia (CLL); chronic myeloid (granulocytic) leukemia (CML); chronic myelomonocytic leukemia (CMML); hairy cell leukemia; and polycythemia vera and myeloproliferative neoplasms including myelofibrosis polycythemia vera and essential thrombocythemia.

Lymphoma

There are two main types of lymphoma—Hodgkin's disease and non-Hodgkin's lymphoma. Hodgkin's disease, also known as Hodgkin's lymphoma, is a special form of lymphoma in which a particular cell known as the Reed Sternberg (R-S) cell occurs. This cell is not usually found in other lymphomas.

The cause for Hodgkin's disease is unknown. Hodgkin's disease, like other cancers, is not infectious and cannot be passed onto other people. It is not inherited. The first symptom of Hodgkin's disease is usually a painless swelling in the neck, armpits or groin. Other symptoms may include night sweats or unexplained fever, weight loss and tiredness, cough or breathlessness, and persistent itch all over the body.

There are about 20 different types of non-Hodgkin's lymphoma. Non-Hodgkin's lymphomas are categorized according to their appearance under the microscope and the cell type (B-cell or T-cell). Risk factors include old age, female, weakened immune system, human T-lymphotropic virus type 1 (HTLV-1) and Epstein-Barr virus infection, and exposure to chemicals such as pesticides, solvents, and fertilizers.

Myeloma

Myeloma is a malignant tumor composed of plasma cells of the type normally found in the bone marrow. Myeloma cells tend to collect in the bone marrow and in the hard, outer part of bones. Sometimes they collect in only one bone and form a single mass, or tumor, called a plasmacytoma. In most cases, however, the myeloma cells collect in many bones, often forming many tumors and causing other problems. When this happens, the disease is called multiple myeloma such as, but not limited to, giant cell myeloma, indolent myeloma, localized myeloma, multiple myeloma, plasma cell myeloma, sclerosing myeloma, solitary myeloma, smoldering multiple myeloma, nonsecretary myeloma, osteosclerotic myeloma, plasma cell leukemia, solitary plasmacytoma, and extramedullary plasmacytoma.

Myelodysplastic Syndromes

Myelodysplastic syndromes are disorders in which the bone marrow produces ineffective and abnormal looking cells on one or more types (white blood cells, red blood cells or platelets). The majority of patients are men over sixty. Secondary myelodysplastic syndromes are seen following the use of chemotherapy and irradiation.

Signs and symptoms depend on the types of cells that are affected. Abnormal white cells make people more susceptible to infections; abnormal platelets make people more susceptible to bruising and spontaneous hemorrhages; and abnormal red blood cells causes anemia and fatigue.

While chemotherapy and radiation are useful in the treatment of hematological malignancies, there is a continued need to find better treatment modalities and approaches to manage the disease that are more effective and less toxic, especially when clinical oncologists are giving increased attention to the quality of life of cancer patients. The present invention provides an alternative approach to hematological malignancies therapy and management of the disease by using an oral composition comprising arsenic trioxide.

Arsenic

Arsenic has been used medicinally for over 2,000 years. In the 18th century, a solution of arsenic trioxide (empirical formula $As_2O_3$) in 1% w/v potassium bicarbonate (Fowler's solution) was developed to treat a variety of infectious and malignant diseases. Its efficacy in suppressing white cells was first described in 1878 (Kwong Y. L. et al. Delicious poison: arsenic trioxide for the treatment of leukemia, Blood 1997; 89:3487-8). Arsenic trioxide was therefore used to treat chronic myelogenous leukemia, until more potent cytotoxic drugs superseded it in the 1940s. However, there was a resurgence of interest in such therapy, when arsenic trioxide was found to induce apoptosis and differentiation in acute promyelocytic leukemia (APL) cells (Chen G. Q. et al. Use of arsenic trioxide ($As_2O_3$) in the treatment of acute promyelocytic leukemia (APL): I. $As_2O_3$ exerts dose-dependent dual effect on APL cells in vitro and in vivo, Blood 1997; 89:3345-53; Soignet S. L. et al. United States multicenter study of arsenic trioxide in relapsed acute promyelocytic leukemia. J Clin Oncol. 2001; 19:3852-60). The clinical implications of these in vitro observations have since been verified, as arsenic trioxide induces remissions in over 90% of such patients (Shen Z. X. et al. Use of arsenic trioxide ($As_2O_3$) in the treatment of acute promyelocytic leukemia (APL): II. Clinical efficacy and pharmacokinetics in relapsed patients, Blood 1997; 89:3354-60; Soignet S. L. et al. Complete remission after treatment of acute promyelocytic leukemia with arsenic trioxide, N Engl J Med 1998; 339:1341-8; Niu C. et al., Studies on treatment of acute promyelocytic leukemia with arsenic trioxide: remission induction, follow-up and molecular monitoring in 11 newly diagnosed and 47 relapsed acute promyelocytic leukemia patients, Blood 1999; 94:3315-24).

A typical course of arsenic trioxide involves daily intravenous (IV) administration for 4 to 8 weeks and the attendant inconvenience, risks and expense of maintaining suitable vascular access and prolonged hospitalization. Currently, there is no FDA-approved oral arsenic trioxide for clinical use. Fowler's solution is no longer detailed in modem pharmacopoeias or listed in formularies (1941, Arsenum. Martindale, The Extra Pharmacopoeia 22:209-15; British Pharmacopoeia. London: Her Majesty's Stationery Office, 1988; Appendix 1A, p A12). Formulation comprising arsenic that could be orally administered could therefore offer distinct advantages.

The inventors of the present invention have arrived at a novel formulation that comprises a lyophilized composition comprising arsenic that can be orally administered. The inventors have developed a method for making such novel formulation comprising lyophilized composition comprising arsenic. The lyophilized powder comprising arsenic is amenable to oral administration in patients, for example, via capsules and tablets.

$As_2O_3$ powder is sparingly and extremely slowly soluble in cold water; even in boiling water it is only soluble in a 1:15 ratio (Arsenic Trioxide, In: Budavari S O'Neil M J (Eds), The Merck Index. An encyclopedia of chemicals, drugs and biologicals. NJ: Merck & Co., Inc. 11th Ed., Rahway, N.J., USA. 1989. Monograph 832, p 127). As a result, and because of other problems described previously, it has not been formulated as an orally available composition.

SUMMARY

The present invention addresses this issue of insolubility and the lack of bioavailability of $As_2O_3$ and provides a lyophilized composition comprising arsenic that makes it bioavailable. The arsenic is introduced as $As_2O_3$ powder, which is then solubilized and lyophilized as described infra. More specifically, this invention relates to a lyophilized composition comprising arsenic, in which the arsenic is present as one or more salt of arsenic, and/or a solvate thereof, and/or $As_2O_3$, and/or one or more arsenic compounds.

Thus, as described herein, by "lyophilized composition comprising arsenic" (LCCA) is meant a composition that comprises arsenic as one or more of its salts, and/or a solvate thereof, and/or arsenic trioxide and/or any other compound comprising arsenic, said composition having resulted from applying the method steps of the present invention describing infra. The lyophilized composition comprising arsenic, alternatively, may be addressed herein as lyophilized arsenic trioxide or lyophilized $As_2O_3$ (LAT).

Clearly, the present invention envisions making this "lyophilized composition comprising arsenic" through other methods.

Stated another way, the independent lyophilized composition comprising arsenic is one aspect of the present invention. In one aspect, this invention also relates to the method of making the LCCA. In another aspect this invention also relates to an oral formulation comprising the LCCA. In yet another aspect, this invention relates to the method of making such oral formulation. This invention also relates to a pharmaceutical composition in a solid dosage form suitable for oral administration, the composition comprising lyophilized composition comprising arsenic. This invention further relates to a pharmaceutical composition in a solid dosage form suitable for oral administration, the composition comprising the LCCA, at least one bulking agent, and at least one lubricant. In one aspect, this invention also relates to a kit comprising the pharmaceutical composition comprising the LCCA. In yet another aspect, this invention relates to a method of treating malignancies, such as hematological malignancies, in a patient in need thereof, comprising the step of administering to the patient a therapeutically effective amount of the pharmaceutical composition comprising the LCCA.

Embodiments—Methods of Making Lyophilized Compositions Comprising Arsenic

This invention relates to a method for preparing lyophilized composition comprising arsenic (LCCA), said method comprising: (A) solubilizing $As_2O_3$ powder in an aqueous medium to form an $As_2O_3$ solution; and (B) lyophilizing said $As_2O_3$ solution. In one embodiment, said solubilizing $As_2O_3$ powder in an aqueous medium comprises: (I) adding an alkalizing agent to the $As_2O_3$ powder in a vessel, with or without stirring and with or without addition of water, to render a pH of about 12 or higher; (II) adding an acid to said vessel, with or without stirring and with or without addition of water, to adjust the pH to from about 7 to about 8; (III) optionally, adding a surfactant to said vessel, with or without stirring and with or without addition of water, and (IV) optionally, adding water to said vessel to generate an $As_2O_3$ solution with or without stirring. In another embodiment, for the methods described thus far in this section, said alkalizing agent comprises sodium hydroxide (NaOH), sodium carbonate ($Na_2CO_3$), or a mixture thereof. In yet another embodiment, the amount of said alkalizing agent added in the methods described above, is about 10% to about 100% the amount of the $As_2O_3$ powder.

In one embodiment of the invention, for the methods described previously in this section, said acid comprises hydrochloric acid (HCl). In another embodiment, said HCl is about 6M HCl. In a further embodiment, said acid is added to said vessel to adjust the pH to about 7.2. In yet another embodiment, for the methods described so far in this section, said surfactant comprises at least one of sodium lauryl sulfate; polyoxyethylene sorbitan monooleate (herein alternatively referred to as "Tween 80®"); betacyclodextrin; poloxamer; tocopheryl polyethylene glycol succinate (TPGS). In another embodiment, said surfactant is added to about 0.5% v/v to about 4.0% v/v, but does not exceed about 50% $As_2O_3$ concentration.

In yet another embodiment of the present invention, for the methods described above in this section, said step of lyophilizing comprises: (A) freezing said $As_2O_3$ solution to generate a frozen $As_2O_3$ product; and (B) drying said $As_2O_3$ product to generate said lyophilized composition comprising arsenic. In another embodiment, for the methods described so far, said freezing step comprises freezing said $As_2O_3$ solution at a temperature in the range of from about −50° C. to about 0° C. In another embodiment, said $As_2O_3$ solution is frozen at about −40° C. for at least about 6 hours. In yet another embodiment, said drying comprises at least one of the following three conditions: (I) drying said $As_2O_3$ product at at least one temperature in the range of from about −40° C. to about 50° C., for the time in the range of from about 5 minutes to about 500 min; (II) drying said frozen $As_2O_3$ by progressively increasing temperature from at least one first temperature in the range of from about −40° C. to about 50° C. to at least one second temperature in the range of from about −40° C. to about 50° C., for the time in the range of from about 5 minutes to about 500 min, wherein said at least one second temperature is higher than said at least one first temperature; and (III) applying vacuum to said frozen $As_2O_3$ product in the range of from about 300 millitorrs to about 1000 millitorrs, for the time in the range of from about 5 minutes to about 500 min.

In one embodiment of the invention, for the methods described so far in this section, said drying step comprises heating said $As_2O_3$ product at about −30° C. and about 800 millitorrs for about 60 minutes; heating said $As_2O_3$ product from the previous step at −20° C. and 500 millitorrs for about 120 minutes; heating said $As_2O_3$ product from the previous step at about −5° C. and about 500 millitorrs for about 120 minutes; heating said $As_2O_3$ product from the previous step at about 10° C. and about 500 millitorrs for about 60 minutes; and heating said $As_2O_3$ product from the previous step at about 25° C. and about 500 millitorrs for the time in the range of from about 180 minutes to 300 minutes. In yet another embodiment, said drying step comprises heating said $As_2O_3$ product to about −30° C. and about 800 millitorrs over about 60 minutes and holding at about −30° C. and about 800 millitorrs for about 60 minutes; heating said $As_2O_3$ product from the previous step to about −20° C. and about 500 millitorrs over about 60 minutes and holding at about −20° C. and about 500 millitorrs for about 120 minutes; heating said $As_2O_3$ product from the previous step to about −5° C. and about 500 millitorrs over about 300 minutes and holding at about −5° C. and about 500 millitorrs for about 120 minutes; heating said $As_2O_3$ product from the previous step to about 10° C. and about 500 millitorrs over about 120 minutes and holding at about 10° C. and about 500 millitorrs for about 60 minutes; and heating said $As_2O_3$ product from the previous step to about 25° C. and about 500 millitorrs over about 60 minutes and holding at about 25° C. and about 500 millitorrs for the time in the range of from about 180 minutes to 300 minutes.

Embodiments—Lyophilized Compositions Comprising Arsenic

This invention relates to a composition comprising lyophilized composition comprising arsenic (LCCA). In one embodiment, such composition further comprising at least one bulking agent, and at least one lubricant. In another embodiment, said composition is prepared by a method comprising: (A) solubilizing $As_2O_3$ powder in an aqueous medium to form an $As_2O_3$ solution; (B) lyophilizing said $As_2O_3$ solution to generate a lyopremix; (C) sifting said lyopremix to generate lyophilized $As_2O_3$ powder; (D) optionally, adding at least one bulking agent to said lyophilized $As_2O_3$ powder; (E) optionally, adding one or more lubricants to said lyophilized $As_2O_3$ powder to generate said oral formulation of $As_2O_3$.

In one embodiment of the invention, for the compositions described previously, said solubilizing $As_2O_3$ powder in an aqueous medium comprises: (I) adding an alkalizing agent to the $As_2O_3$ powder in a vessel, with or without stirring and with or without addition of water, to render a pH of about 12 or higher; (II) adding an acid to said vessel, with or without stirring and with or without addition of water, to adjust the pH to from about 7 to about 8; (III) optionally, adding a surfactant to said vessel, with or without stirring and with or without addition of water, and (IV) optionally, adding water to said vessel to generate an $As_2O_3$ solution with or without stirring. In another embodiment, for the compositions described thus far, said alkalizing agent comprises sodium hydroxide (NaOH), sodium carbonate ($Na_2CO_3$), or a mixture thereof. In yet another embodiment, the amount of said alkalizing agent added in the compositions described above, is about 10% to about 100% the amount of the $As_2O_3$ powder.

In one embodiment of the invention, for the compositions described previously, said acid comprises hydrochloric acid (HCl). In another embodiment, said HCl is about 6M HCl. In a further embodiment, said acid is added to said vessel to adjust the pH to about 7.2. In yet another embodiment, for the compositions described so far, said surfactant comprises at least one of sodium lauryl sulfate; Tween 80®; betacyclodextrin; poloxamer; tocopheryl polyethylene glycol succinate (TPGS). In another embodiment, said surfactant is added to about 0.5% v/v to about 4.0% v/v, but does not exceed about 50% $As_2O_3$ concentration.

In yet another embodiment of the present invention, for the compositions described above, said step of lyophilizing comprises: (A) freezing said $As_2O_3$ solution to generate a frozen $As_2O_3$ product; and (B) drying said $As_2O_3$ product to generate said lyophilized composition comprising arsenic. In another embodiment, for the compositions described so far, said freezing step comprises freezing said $As_2O_3$ solution at a temperature in the range of from about −50° C. to about 0° C. In another embodiment, said $As_2O_3$ solution is frozen at about −40° C. for at least about 6 hours. In yet another embodiment, said drying comprises at least one of the following three conditions: (I) drying said $As_2O_3$ product at at least one temperature in the range of from about −40° C. to about 50° C., for the time in the range of from about 5 minutes to about 500 min; (II) drying said frozen $As_2O_3$ by progressively increasing temperature from at least one first temperature in the range of from about −40° C. to about 50° C. to at least one second temperature in the range of from about −40° C. to about 50° C., for the time in the range of from about 5 minutes to about 500 min, wherein said at least one second temperature is higher than said at least one first temperature; and (III) applying vacuum to said frozen $As_2O_3$ product in the range of from about 300 millitorrs to about 1000 millitorrs, for the time in the range of from about 5 minutes to about 500 min.

In one embodiment of the invention, for the compositions described so far in this section, said drying step comprises heating said $As_2O_3$ product at about −30° C. and about 800 millitorrs for about 60 minutes; heating said $As_2O_3$ product from the previous step at −20° C. and 500 millitorrs for about 120 minutes; heating said $As_2O_3$ product from the previous step at about −5° C. and about 500 millitorrs for about 120 minutes; heating said $As_2O_3$ product from the previous step at about 10° C. and about 500 millitorrs for about 60 minutes; and heating said $As_2O_3$ product from the previous step at about 25° C. and about 500 millitorrs for the time in the range of from about 180 minutes to 300 minutes. In yet another embodiment, said drying step comprises heating said $As_2O_3$ product to about −30° C. and about 800 millitorrs over about 60 minutes and holding at about −30° C. and about 800 millitorrs for about 60 minutes; heating said $As_2O_3$ product from the previous step to about −20° C. and about 500 millitorrs over about 60 minutes and holding at about −20° C. and about 500 millitorrs for about 120 minutes; heating said $As_2O_3$ product from the previous step to about −5° C. and about 500 millitorrs over about 300 minutes and holding at about −5° C. and about 500 millitorrs for about 120 minutes; heating said $As_2O_3$ product from the previous step to about 10° C. and about 500 millitorrs over about 120 minutes and holding at about 10° C. and about 500 millitorrs for about 60 minutes; and heating said $As_2O_3$ product from the previous step to about 25° C. and about 500 millitorrs over about 60 minutes and holding at about 25° C. and about 500 millitorrs for the time in the range of from about 180 minutes to 300 minutes.

In another embodiment of the present invention, for the compositions described previously in this section, said bulking agent comprises mannitol; and/or wherein said one or more lubricants comprises talc and/or magnesium stearate. In another embodiment, said composition is a controlled-release, oral, solid, composition. In one embodiment, the compositions described previously in this section are encapsulated in a capsule.

Embodiments—Methods for Preparing Oral Pharmaceutical Formulation Comprising LCCA This invention relates to a method for preparing an oral pharmaceutical formulation comprising a lyophilized composition comprising arsenic or lyophilized arsenic trioxide ($As_2O_3$), said method comprising: (A) solubilizing $As_2O_3$ powder in an aqueous medium to form an $As_2O_3$ solution; (B) lyophilizing said $As_2O_3$ solution to generate a lyopremix; (C) sifting said lyopremix to generate lyophilized $As_2O_3$ powder; (D) optionally, adding at least one bulking agent to said lyophilized $As_2O_3$ powder; (E) optionally, adding one or more lubricants to said lyophilized $As_2O_3$ powder to generate said oral formulation of $As_2O_3$.

This invention also relates to the method described previously, said solubilizing $As_2O_3$ powder in an aqueous medium comprises: (I) adding an alkalizing agent to the $As_2O_3$ powder in a vessel, with or without stirring and with or without addition of water, to render a pH of about 12 or higher; (II) adding an acid to said vessel, with or without stirring and with or without addition of water, to adjust the pH to from about 7 to about 8; (III) optionally, adding a surfactant to said vessel, with or without stirring and with or without addition of water, and (IV) optionally, adding water to said vessel to generate an $As_2O_3$ solution with or without stirring. In another embodiment, for the methods described thus far in this section, said alkalizing agent comprises sodium hydroxide (NaOH), sodium carbonate ($Na_2CO_3$), or a mixture thereof. In yet another embodiment, the amount of said alkalizing agent added in the methods described above, is about 10% to about 100% the amount of the $As_2O_3$ powder.

In one embodiment of the invention, for the methods described previously in this section, said acid comprises hydrochloric acid (HCl). In another embodiment, said HCl is about 6M HCl. In a further embodiment, said acid is added to said vessel to adjust the pH to about 7.2. In yet another embodiment, for the methods described so far in this section, said surfactant comprises at least one of sodium lauryl sulfate; Tween 80®; betacyclodextrin; poloxamer; tocopheryl polyethylene glycol succinate (TPGS). In another embodiment, said surfactant is added to about 0.5% v/v to about 4.0% v/v, but does not exceed about 50% $As_2O_3$ concentration.

In yet another embodiment of the present invention, for the methods described above in this section, said step of lyophilizing comprises: (A) freezing said $As_2O_3$ solution to generate a frozen $As_2O_3$ product; and (B) drying said $As_2O_3$ product to generate said lyophilized composition comprising arsenic. In another embodiment, for the methods described so far, said freezing step comprises freezing said $As_2O_3$ solution at a temperature in the range of from about −50° C. to about 0° C. In another embodiment, said $As_2O_3$ solution is frozen at about −40° C. for at least about 6 hours. In yet another embodiment, said drying comprises at least one of the following three conditions: (I) drying said $As_2O_3$ product at at least one temperature in the range of from about −40° C. to about 50° C., for the time in the range of from about 5 minutes to about 500 min; (II) drying said frozen $As_2O_3$ by progressively increasing temperature from at least one first temperature in the range of from about −40° C. to about 50° C. to at least one second temperature in the range of from about −40° C. to about 50° C., for the time in the range of from about 5 minutes to about 500 min, wherein said at least one second temperature is higher than said at least one first temperature; and (III) applying vacuum to said frozen $As_2O_3$ product in the range of from about 300 millitorrs to about 1000 millitorrs, for the time in the range of from about 5 minutes to about 500 min.

In one embodiment of the invention, for the methods described so far in this section, said drying step comprises heating said $As_2O_3$ product at about −30° C. and about 800 millitorrs for about 60 minutes; heating said $As_2O_3$ product from the previous step at −20° C. and 500 millitorrs for about 120 minutes; heating said $As_2O_3$ product from the previous step at about −5° C. and about 500 millitorrs for about 120 minutes; heating said $As_2O_3$ product from the previous step at about 10° C. and about 500 millitorrs for about 60 minutes; and heating said $As_2O_3$ product from the previous step at about 25° C. and about 500 millitorrs for the time in the range of from about 180 minutes to 300 minutes. In yet another embodiment, said drying step comprises heating said $As_2O_3$ product to about −30° C. and about 800 millitorrs over about 60 minutes and holding at about −30° C. and about 800 millitorrs for about 60 minutes; heating said $As_2O_3$ product from the previous step to about −20° C. and about 500 millitorrs over about 60 minutes and holding at about −20° C. and about 500 millitorrs for about 120 minutes; heating said $As_2O_3$ product from the previous step to about −5° C. and about 500 millitorrs over about 300 minutes and holding at about −5° C. and about 500 millitorrs for about 120 minutes; heating said $As_2O_3$ product from the previous step to about 10° C. and about 500 millitorrs over about 120 minutes and holding at about 10° C. and about 500 millitorrs for about 60 minutes; and heating said $As_2O_3$ product from the previous step to about 25° C. and about 500 millitorrs over about 60 minutes and holding at about 25° C. and about 500 millitorrs for the time in the range of from about 180 minutes to 300 minutes.

In another embodiment of the present invention, for the methods described previously in this section, said bulking agent comprises mannitol; and/or wherein said one or more lubricants comprises talc and/or magnesium stearate. In another embodiment, methods described previously further comprise the step of filling a capsule with said oral formulation.

Embodiments—Oral Pharmaceutical Formulation Comprising LCCA

This invention relates to a pharmaceutical composition in a solid dosage form suitable for oral administration, said composition comprising lyophilized composition comprising arsenic. In one embodiment, such pharmaceutical composition further comprises at least one bulking agent, and at least one lubricant. In yet another embodiment, the pharmaceutical compositions described so far in this section is prepared by a method comprising: (A) solubilizing $As_2O_3$ powder in an aqueous medium to form an $As_2O_3$ solution; (B) lyophilizing said $As_2O_3$ solution to generate a lyopremix; (C) sifting said lyopremix to generate lyophilized $As_2O_3$ powder; (D) optionally, adding at least one bulking agent to said lyophilized $As_2O_3$ powder; (E) optionally, adding one or more lubricants to said lyophilized $As_2O_3$ powder to generate said oral formulation of $As_2O_3$.

In one embodiment of the invention, for the pharmaceutical compositions described previously in this section, said solubilizing $As_2O_3$ powder in an aqueous medium comprises: (I) adding an alkalizing agent to the $As_2O_3$ powder in a vessel, with or without stirring and with or without addition of water, to render a pH of about 12 or higher; (II) adding an acid to said vessel, with or without stirring and with or without addition of water, to adjust the pH to from about 7 to about 8; (III) optionally, adding a surfactant to said vessel, with or without stirring and with or without addition of water, and (IV) optionally, adding water to said vessel to generate an $As_2O_3$ solution with or without stirring. In another embodiment, for the compositions described thus far, said alkalizing agent comprises sodium hydroxide (NaOH), sodium carbonate ($Na_2CO_3$), or a mixture thereof. In yet another embodiment, the amount of said alkalizing agent added in the pharmaceutical compositions described above, is about 10% to about 100% the amount of the $As_2O_3$ powder.

In one embodiment of the invention, for the pharmaceutical compositions described previously, said acid comprises hydrochloric acid (HCl). In another embodiment, said HCl is about 6M HCl. In a further embodiment, said acid is added to said vessel to adjust the pH to about 7.2. In yet another embodiment, for the pharmaceutical compositions described so far, said surfactant comprises at least one of sodium lauryl sulfate; Tween 80®; betacyclodextrin; poloxamer; tocopheryl polyethylene glycol succinate (TPGS). In another embodiment, said surfactant is added to about 0.5% v/v to about 4.0% v/v, but does not exceed about 50% $As_2O_3$ concentration.

In yet another embodiment of the present invention, for the pharmaceutical compositions described above, said step of lyophilizing comprises: (A) freezing said $As_2O_3$ solution to generate a frozen $As_2O_3$ product; and (B) drying said $As_2O_3$ product to generate said lyophilized composition comprising arsenic. In another embodiment, for the compositions described so far, said freezing step comprises freezing said $As_2O_3$ solution at a temperature in the range of from about −50° C. to about 0° C. In another embodiment, said $As_2O_3$ solution is frozen at about −40° C. for at least about 6 hours. In yet another embodiment, said drying comprises at least one of the following three conditions: (I) drying said $As_2O_3$ product at at least one temperature in the range of from about −40° C. to about 50° C., for the time in the range of from about 5 minutes to about 500 min; (II) drying said frozen $As_2O_3$ by progressively increasing temperature from at least one first temperature in the range of from about −40° C. to about 50° C. to at least one second temperature in the range of from about −40° C. to about 50° C., for the time in the range of from about 5 minutes to about 500 min, wherein said at least one second temperature is higher than said at least one first temperature; and (III) applying vacuum to said frozen $As_2O_3$ product in the range of from about 300 millitorrs to about 1000 millitorrs, for the time in the range of from about 5 minutes to about 500 min.

In one embodiment of the invention, for the pharmaceutical compositions described so far, said drying step comprises heating said $As_2O_3$ product at about −30° C. and about 800 millitorrs for about 60 minutes; heating said $As_2O_3$ product from the previous step at −20° C. and 500 millitorrs for about 120 minutes; heating said $As_2O_3$ product from the previous step at about −5° C. and about 500 millitorrs for about 120 minutes; heating said $As_2O_3$ product from the previous step at about 10° C. and about 500 millitorrs for about 60 minutes; and heating said $As_2O_3$ product from the previous step at about 25° C. and about 500 millitorrs for the time in the range of from about 180 minutes to 300 minutes. In yet another embodiment, said drying step comprises heating said $As_2O_3$ product to about −30° C. and about 800 millitorrs over about 60 minutes and holding at about −30° C. and about 800 millitorrs for about 60 minutes; heating said $As_2O_3$ product from the previous step to about −20° C. and about 500 millitorrs over about 60 minutes and holding at about −20° C. and about 500 millitorrs for about 120 minutes; heating said $As_2O_3$ product from the previous step to about −5° C. and about 500 millitorrs over about 300 minutes and holding at about −5° C. and about 500 millitorrs for about 120 minutes; heating said $As_2O_3$ product from the previous step to about 10° C. and about 500 millitorrs over about 120 minutes and holding at about 10° C. and about 500 millitorrs for about 60 minutes; and heating said $As_2O_3$ product from the previous step to about 25° C. and about 500 millitorrs over about 60 minutes and holding at about 25° C. and about 500 millitorrs for the time in the range of from about 180 minutes to 300 minutes.

In another embodiment of the present invention, for the pharmaceutical compositions described previously in this section, said bulking agent comprises mannitol; and/or wherein said one or more lubricants comprises talc and/or magnesium stearate. In another embodiment, said pharmaceutical composition is a controlled-release, oral, solid, composition. In one embodiment, the pharmaceutical compositions described previously in this section are encapsulated in a capsule.

In another set of embodiments, the present invention also relates to a capsule comprising about 1 mg, about 5 mg, 10 mg, or about 20 mg of the pharmaceutical composition previously described in this section. This invention further relates to a kit comprising the pharmaceutical composition described in this section, and instructions for use of the same.

Embodiments—Administration of Pharmaceutical Composition to Patients

This invention relates to a method of orally administering to a subject, a pharmaceutical composition comprising lyophilized composition comprising arsenic, comprising the steps of providing said pharmaceutical composition, and orally administering said pharmaceutical composition to said subject. This invention further relates to a method of treating malignancies such as a cancer or a tumor in a patient in need thereof, comprising the step of administering to the patient a therapeutically effective amount of the pharmaceutical composition comprising lyophilized composition comprising arsenic.

In yet another embodiment, this invention relates to the methods described previously in this section wherein said cancer is a hematological malignancy. In another embodiment, said hematological malignancy is at least one of acute myeloid leukemia; acute nonlymphocytic leukemia; myeloblastic leukemia, promyelocytic leukemia; chronic myelomonocytic leukemia; monocytic leukemia; erythroleukemia; acute neutrophilic leukemia; myelodysplastic syndrome; acute promyelocytic leukemia; chronic lymphocytic leukemia; chronic myeloid leukemia; hairy cell leukemia; myeloproliferative neoplasms; Hodgkin's lymphoma; non-Hodgkin's lymphoma; myeloma; giant cell myeloma; indolent myeloma; localized myeloma; multiple myeloma; plasma cell myeloma; sclerosing myeloma; solitary myeloma; smoldering multiple myeloma; nonsecretary myeloma; osteosclerotic myeloma; plasma cell leukemia; solitary plasmacytoma; and extramedullary plasmacytoma.

In another embodiment, for the methods described thus far in this section, said hematological malignancy is acute promyelocytic leukemia (APL). In one embodiment, said APL is newly diagnosed APL. In another embodiment, said APL is relapsed or refractory APL.

In one embodiment, in the methods of treatment described previously in this section, said myeloproliferative neoplasm is one of myelofibrosis polycythemia vera and essential thrombocythemia.

In one embodiment of the present invention, for the methods described in this section, said pharmaceutical composition is administered daily. In another embodiment, said wherein said pharmaceutical composition is administered in a single dosage range of about 1 mg to about 50 mg. In a further embodiment, said pharmaceutical composition is administered in a single dosage range of about 0.1 mg/kg body weight to about 0.3 mg/kg body weight.

In another embodiment, for the methods described previously in this section, said patient was previously treated or is currently being treated with chemotherapy and/or radiation. In another embodiment, said patient is further administered one or more chemotherapeutic agents. In one embodiment of this method, said chemotherapeutic agent is administered before, after, or simultaneously with said pharmaceutical composition.

Embodiments—Improvement in Physical/Chemical Characteristics of the Formulation Powder This invention relates to a method for increasing the surface area of original API powder comprising arsenic trioxide, from about 2× to about 80× comprising the steps of: (A) solubilizing $As_2O_3$ powder in an aqueous medium to form an $As_2O_3$ solution, comprising the steps of: (I) adding an alkalizing agent to the $As_2O_3$ powder in a vessel, with or without stirring and with or without addition of water, to render a pH of about 12 or higher; (II) adding an acid to said vessel, with or without stirring and with or without addition of water, to adjust the pH to from about 7 to about 8; (III) optionally, adding a surfactant to said vessel, with or without stirring and with or without addition of water, and (IV) optionally, adding water to said vessel to generate an $As_2O_3$ solution with or without stirring; and (B) lyophilizing said $As_2O_3$ solution comprising the steps of: (V) freezing said $As_2O_3$ solution to generate a frozen $As_2O_3$ product; and (VI) drying said $As_2O_3$ product to generate said lyophilized composition comprising arsenic.

This invention also relates to a method for increasing the solubility of arsenic trioxide powder in water or in alcohol by about 2× to about 30×, said method comprising the steps of: (A) solubilizing $As_2O_3$ powder in an aqueous medium to form an $As_2O_3$ solution, comprising the steps of: (I) adding an alkalizing agent to the $As_2O_3$ powder in a vessel, with or without stirring and with or without addition of water, to render a pH of about 12 or higher; (II) adding an acid to said vessel, with or without stirring and with or without addition of water, to adjust the pH to from about 7 to about 8; (III) optionally, adding a surfactant to said vessel, with or without stirring and with or without addition of water, and (IV) optionally, adding water to said vessel to generate an $As_2O_3$ solution with or without stirring; and (B) lyophilizing said $As_2O_3$ solution comprising the steps of: (V) freezing said $As_2O_3$ solution to generate a frozen $As_2O_3$ product; and (VI) drying said $As_2O_3$ product to generate said lyophilized composition comprising arsenic.

This invention also relates to a method for increasing the dissolution of a pharmaceutical composition comprising arsenic, by at least five times over the original API comprising arsenic trioxide, comprising the steps of: (A) solubilizing $As_2O_3$ powder in an aqueous medium to form an $As_2O_3$ solution, comprising the steps of: (I) adding an alkalizing agent to the $As_2O_3$ powder in a vessel, with or without stirring and with or without addition of water, to render a pH of about 12 or higher; (II) adding an acid to said vessel, with or without stirring and with or without addition of water, to adjust the pH to from about 7 to about 8; (III) optionally, adding a surfactant to said vessel, with or without stirring and with or without addition of water, and (IV) optionally, adding water to said vessel to generate an $As_2O_3$ solution with or without stirring; and (B) lyophilizing said $As_2O_3$ solution comprising the steps of: (V) freezing said $As_2O_3$ solution to generate a frozen $As_2O_3$ product; and (VI) drying said $As_2O_3$ product to generate said lyophilized composition comprising arsenic.

This invention also relates to a method for providing oral bioavailability of arsenic to a subject, wherein said oral bioavailability is in the range of from about 50% to about 100% of that of the intravenous administration of a pharmaceutical composition comprising arsenic, said method comprising the steps of: (A) solubilizing $As_2O_3$ powder in an aqueous medium to form an $As_2O_3$ solution, comprising the steps of: (I) adding an alkalizing agent to the $As_2O_3$ powder in a vessel, with or without stirring and with or without addition of water, to render a pH of about 12 or higher; (II) adding an acid to said vessel, with or without stirring and with or without addition of water, to adjust the pH to from about 7 to about 8; (III) optionally, adding a surfactant to said vessel, with or without stirring and with or without addition of water, and (IV) optionally, adding water to said vessel to generate an $As_2O_3$ solution with or without stirring; and (B) lyophilizing said $As_2O_3$ solution comprising the steps of: (V) freezing said $As_2O_3$ solution to generate a frozen $As_2O_3$ product; and (VI) drying said $As_2O_3$ product to generate said lyophilized composition comprising arsenic.

This invention also relates to the composition comprising lyophilized composition comprising arsenic (LCCA), wherein said lyophilized composition comprising arsenic comprises particles in the D(90) size range of from about 2 micron to 10 micron. In another embodiment, said lyophilized composition comprising arsenic comprises particles having a D(90) size that is from about 10-times to about 50-times smaller than the particle size of the original API powder comprising arsenic trioxide. In yet another embodiment, said lyophilized composition comprising arsenic comprises particles having a BET surface area in the range of from about 0.5 $m^2/g$ to 5 $m^2/g$. In yet another embodiment, said lyophilized composition comprising arsenic comprises particles having a BET surface area that is from about 5× to about 80× more than the surface area of the original API powder comprising arsenic trioxide. In yet another embodiment, said lyophilized composition comprising arsenic is from about 2× to about 30× times more soluble in cold water or an alcohol than the original API powder comprising arsenic trioxide. In another embodiment, said lyophilized composition comprising arsenic is soluble in cold water or alcohol in the range of from about 4 g/100 g to about 60 g/100 g of the lyophilized composition to the cold water or the alcohol.

In one embodiment, the present invention relates to pharmaceutical compositions described in previous section, wherein the dissolution of said pharmaceutical compositions as measured by ICP-OES is from about 5× to about 15× of that of the original API powder comprising arsenic trioxide.

This invention also relates to an oral dosage form in the form of a capsule which weighs 100 units and comprises: (I) lyophilized composition comprising arsenic, at an amount that provides 10 units of arsenic trioxide and 5 units sodium lauryl sulfate; (II) mannitol at an amount of 73 units; (III) talc at an amount of 1; and (IV) magnesium stearate at an amount of 1 mg; which brings the total weight of the composition to 100 units. In one set of embodiment of the present invention, said capsule weighs 10 mg, 50 mg, 100 mg, or 200 mg.

For example, an oral dosage form in the form of a capsule which weighs 10 mg and comprises:

(I) lyophilized composition comprising arsenic, at an amount that provides 1 mg of arsenic trioxide and 0.5 mg sodium lauryl sulfate;

(II) mannitol at an amount of 7.3 mg;

(III) talc at an amount of 0.1 mg; and (IV) magnesium stearate at an amount of 0.1 mg that brings the total weight of the composition to 10 mg.

Similarly, an oral dosage form in the form of a capsule which weighs 50 mg and comprises:

(I) lyophilized composition comprising arsenic, at an amount that provides 5 mg of arsenic trioxide and 2.5 mg sodium lauryl sulfate;

(II) mannitol at an amount of 36.5 mg;

(III) talc at an amount of 0.5 mg; and (IV) magnesium stearate at an amount of 0.5 mg that brings the total weight of the composition to 50 mg.

In another example, an oral dosage form in the form of a capsule which weighs 100 mg and comprises:

(I) lyophilized composition comprising arsenic, at an amount that provides 10 mg of arsenic trioxide and 5 mg sodium lauryl sulfate;

(II) mannitol at an amount of 73 mg;

(III) talc at an amount of 1 mg; and (IV) magnesium stearate at an amount of 1 mg that brings the total weight of the composition to 100 mg.

In yet another example, an oral dosage form in the form of a capsule which weighs 200 mg and comprises:

(I) lyophilized composition comprising arsenic, at an amount that provides 20 mg of arsenic trioxide and 10 mg sodium lauryl sulfate;

(II) mannitol at an amount of 146 mg;

(III) talc at an amount of 2 mg; and (IV) magnesium stearate at an amount of 2 mg that brings the total weight of the composition to 200 mg.

These, and other aspects of the present invention are described in detail infra.

DESCRIPTION OF THE INVENTION

Figure 1:
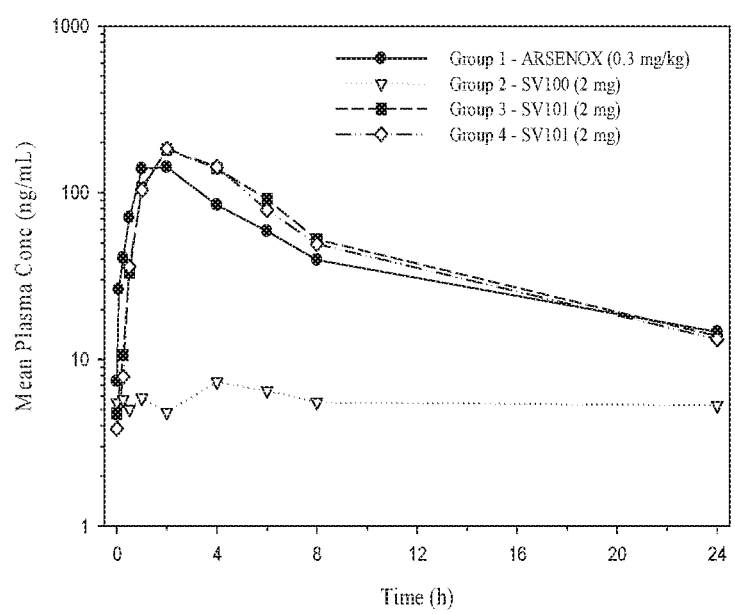
FIG. 1 shows pharmacokinetic analysis in dogs of novel lyophilized formulation comprising Arsenic and comparison with reference arsenic trioxide.

This invention relates to a method for preparing lyophilized composition comprising arsenic (LCCA), said method comprising: (A) solubilizing $As_2O_3$ powder in an aqueous medium to form an $As_2O_3$ solution; and (B) lyophilizing said $As_2O_3$ solution. In one embodiment, said solubilizing $As_2O_3$ powder in an aqueous medium comprises: (I) adding an alkalizing agent to the $As_2O_3$ powder in a vessel, with or without stirring and with or without addition of water, to render a pH of about 12 or higher; (II) adding an acid to said vessel, with or without stirring and with or without addition of water, to adjust the pH to from about 7 to about 8; (III) optionally, adding a surfactant to said vessel, with or without stirring and with or without addition of water, and (IV) optionally, adding water to said vessel to generate an $As_2O_3$ solution with or without stirring.

In yet another embodiment of the present invention, for the methods described above in this section, said step of lyophilizing comprises: (A) freezing said $As_2O_3$ solution to generate a frozen $As_2O_3$ product; and (B) drying said $As_2O_3$ product to generate said lyophilized composition comprising arsenic. In another embodiment, for the methods described so far, said freezing step comprises freezing said $As_2O_3$ solution at a temperature in the range of from about −50° C. to about 0° C. In another embodiment, said $As_2O_3$ solution is frozen at about −40° C. for at least about 6 hours.

This invention also relates to a composition comprising lyophilized composition comprising arsenic (LCCA). In one embodiment, such composition further comprising at least one bulking agent, and at least one lubricant. In another embodiment, said composition is prepared by a method comprising: (A) solubilizing $As_2O_3$ powder in an aqueous medium to form an $As_2O_3$ solution; (B) lyophilizing said $As_2O_3$ solution to generate a lyopremix; (C) sifting said lyopremix to generate lyophilized $As_2O_3$ powder; (D) optionally, adding at least one bulking agent to said lyophilized $As_2O_3$ powder; (E) optionally, adding one or more lubricants to said lyophilized $As_2O_3$ powder to generate said oral formulation of $As_2O_3$.

In another embodiment of the present invention, for the compositions described previously in this section, said bulking agent comprises mannitol; and/or wherein said one or more lubricants comprises talc and/or magnesium stearate. In another embodiment, said composition is a controlled-release, oral, solid, composition. In one embodiment, the compositions described previously in this section are encapsulated in a capsule.

This invention also relates to a method for preparing an oral pharmaceutical formulation comprising a lyophilized composition comprising arsenic or lyophilized arsenic trioxide ($As_2O_3$), said method comprising: (A) solubilizing $As_2O_3$ powder in an aqueous medium to form an $As_2O_3$ solution; (B) lyophilizing said $As_2O_3$ solution to generate a lyopremix; (C) sifting said lyopremix to generate lyophilized $As_2O_3$ powder; (D) optionally, adding at least one bulking agent to said lyophilized $As_2O_3$ powder; (E) optionally, adding one or more lubricants to said lyophilized $As_2O_3$ powder to generate said oral formulation of $As_2O_3$. This invention relates to a pharmaceutical composition in a solid dosage form suitable for oral administration, said composition comprising lyophilized composition comprising arsenic. In one embodiment, such pharmaceutical composition further comprises at least one bulking agent, and at least one lubricant. In yet another embodiment, the pharmaceutical compositions described so far in this section is prepared by the method described herein. In another embodiment of the present invention, for the pharmaceutical compositions described previously in this section, said bulking agent comprises mannitol; and/or wherein said one or more lubricants comprises talc and/or magnesium stearate. In another embodiment, said pharmaceutical composition is a controlled-release, oral, solid, composition. In one embodiment, the pharmaceutical compositions described previously in this section are encapsulated in a capsule.

In another set of embodiments, the present invention also relates to a capsule comprising about 1 mg, about 5 mg, 10 mg, or about 20 mg of the pharmaceutical composition previously described in this section. This invention further relates to a kit comprising the pharmaceutical composition described in this section, and instructions for use of the same.

This invention relates to a method of orally administering to a subject, a pharmaceutical composition comprising lyophilized composition comprising arsenic, comprising the steps of providing said pharmaceutical composition, and orally administering said pharmaceutical composition to said subject. This invention further relates to a method of treating a cancer in a patient in need thereof, comprising the step of administering to the patient a therapeutically effective amount of the pharmaceutical composition comprising lyophilized composition comprising arsenic.

This invention relates to a method for increasing the surface area of original API powder comprising arsenic trioxide, from about 5× to about 80×; for increasing the solubility of arsenic trioxide powder in water or in alcohol by about 2× to about 30×; for increasing the dissolution of a pharmaceutical composition comprising arsenic, by at least five times over the original API; for providing oral bioavailability of arsenic to a subject, wherein said oral bioavailability is in the range of from about 50% to about 100% of that of the intravenous administration of a pharmaceutical composition comprising arsenic; and for reducing the particles in the D(90) size range to from about 2 micron to about 10 micron.

This invention also relates to an oral dosage form in the form of a capsule which weighs 100 units and comprises: (I) lyophilized composition comprising arsenic, at an amount that provides 10 units of arsenic trioxide and 5 units sodium lauryl sulfate; (II) mannitol at an amount of 73 units; (III) talc at an amount of 1; and (IV) magnesium stearate at an amount of 1 mg; which brings the total weight of the composition to 100 units. In one set of embodiment of the present invention, said capsule weighs 10 mg, 50 mg, 100 mg, or 200 mg.

Methods of Use

Use in Subjects with Hematological Malignancies

The present invention further provides methods of using the orally administered lyophilized composition comprising arsenic. In one embodiment, the lyophilized composition comprising arsenic is used as a medicament for treatment of hematological malignancies (e.g., leukemia, Hodgkin's disease, non-Hodgkin's lymphoma, and myeloma). The methods comprise administering an effective amount of the lyophilized composition comprising arsenic to a subject in need. The lyophilized composition comprising arsenic may be administered orally, in a lyophilized form, or enterally through a feeding tube. As used herein, the term "an effective amount" means an amount sufficient to provide a therapeutic or healthful benefit in the context of hematological malignancies.

In one embodiment, the lyophilized composition comprising arsenic can produce a healthful benefit in a subject suffering from hematological malignancies. Preferably, the subject is a human being. The subject in need is one who is diagnosed with hematological malignancies, with or without metastasis, at any stage of the disease. As used herein, the term "hematological malignancies" include but are not limited to leukemia, lymphoma, and myeloma. As used herein, the term "leukemia" includes but is not limited to acute lymphocytic leukemia (ALL); acute myeloid leukemia (AML) (sometimes called acute nonlymphocytic leukemia (ANLL)) such as myeloblastic, promyelocytic, myelomonocytic, monocytic, erythroleukemia leukemias and myelodysplastic syndrome; chronic lymphocytic leukemia (CLL); chronic myeloid (granulocytic) leukemia (CIVIL); chronic myelomonocytic leukemias (CMML); hairy cell leukemia; and polycythemia vera. As used herein, the term "lymphoma" includes but is not limited to Hodgkin's disease and non-Hodgkin's lymphoma. As used herein, the term "myeloma" includes but is not limited to giant cell myeloma, indolent myeloma, localized myeloma, multiple myeloma, plasma cell myeloma, sclerosing myeloma, solitary myeloma, smoldering multiple myeloma, nonsecretary myeloma, osteosclerotic myeloma, plasma cell leukemia, solitary plasmacytoma, and extramedullary plasmacytoma.

The subject may be a patient who is receiving concurrently other treatment modalities against the hematological malignancies. The subject can be a patient with hematological malignancies who had undergone a regimen of treatment (e.g., chemotherapy and/or radiation) and whose cancer is regressing. The subject may be a patient with hematological malignancies who had undergone a regimen of treatment and who appears to be clinically free of the hematological malignancies. The lyophilized composition comprising arsenic of the invention can be orally administered adjunctively with any of the treatment modalities, such as but not limited to chemotherapy and/or radiation. For example, the arsenic trioxide composition can be used in combination with one or more chemotherapeutic or immunotherapeutic agents, such as amsacrine (AMSA), busulfan (Myleran®), chlorambucil (Leukeran®), cladribine (2-chlorodeoxyadenosine; "2-CDA"; Leustatin®), cyclophosphamide (Cytoxan®), cytarabine (ara-C; Cytosar-U®), daunorubicin (Cerubidine®), doxorubicin (Adriamycin®), etoposide (VePesid®), fludarabine phosphate (Fludara®), hydroxyurea (Hydrea®), idarubicin (Idamycin®), L-asparaginase (Elspar®), methotrexate sodium plus 6-mercaptopurine (6-MP; Purinethol®), mitoxantrone (Novantrone®), pentostatin (2-deoxycoformycin; "DCF"; Nipent®), prednisone, retinoic acid (ATRA), vincristine sulfate (Oncovin®), 6-thioguanine (Tabloid®), cyclosporin A, Taxol®), Cisplatin®, Carboplatin®, Doxil®, Topotecan®, Methotrexate®, Bleomycin®, and Epirubicin®. The arsenic trioxide composition can also be used after other regimen(s) of treatment is concluded.

The subject may be one who has not yet been diagnosed with hematological malignancies but are predisposed to or at high risk of developing hematological malignancies as a result of genetic factors and/or environmental factors.

Depending on the subject, the therapeutic and healthful benefits range from inhibiting or retarding the growth of the hematological malignancies and/or the spread of the hematological malignancies to other parts of the body (i.e., metastasis), palliating the symptoms of the cancer, improving the probability of survival of the subject with the cancer, prolonging the life expectancy of the subject, improving the quality of life of the subject, and/or reducing the probability of relapse after a successful course of treatment (e.g., chemotherapy, radiation). The symptoms associated with hematological malignancies include but are not limited to a weakened immune system, infections, fevers, decrease in red blood cells and platelets, weakness, fatigue, loss of appetite, loss of weight, swollen or tender lymph nodes, liver, or spleen, easy bleeding or bruising, tiny red spots (called petechiae) under the skin, swollen or bleeding gums, sweating (especially at night), bone or joint pain, headaches, vomiting, confusion, loss of muscle control, and seizures.

In particular, the invention provides a method for complete remission of the hematological malignancies in a subject, such as a human, comprising administering orally to the subject an arsenic trioxide composition of the invention. In other embodiments, the invention provides at least 10%, 20%, 30%, 40%, 50%, 60%, 70%, 80%, 90%, and 95% remission of the hematological malignancy. The invention also provide a method for prolonging the time of survival of a subject inflicted with hematological malignancies, preferably a human patient, comprising administering orally to the subject a lyophilized composition comprising arsenic of the invention.

The effective dose will vary with the subject treated and the route of administration. The effective dose for the subject will also vary with the condition to be treated and the severity of the condition to be treated. The dose, and perhaps the dose frequency, will also vary according to the age, body weight, and response of the individual subject. In general, the total daily dose range of the lyophilized composition comprising arsenic for a subject inflicted with hematological malignancies in mg is as follows: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 mg per day. Depending upon the need of the patient it can be higher, for example, 60, 70, 80, 90, and 100 mg/day, or any intermediate dosage numbers therebetween. The lyophilized premix comprising arsenic composition is administered to the subject orally.

The length of time for a course of treatment should be at least 1 day, at least 2 days, at least 3 days, at least 4 days, at least 5 days, at least 6 days, at least 1 week, at least 2 weeks, at least 3 weeks, at least 4 weeks, at least 5 weeks, at least 7 weeks, at least 10 weeks, at least 13 weeks, at least 15 weeks, at least 20 weeks, at least 6 months, at least 1 year, or at least two years. It may be necessary to use dosages outside these ranges in some cases as will be apparent to those skilled in the art. In certain embodiments, the lyophilized composition comprising arsenic can be administered for a period of time until the symptoms are under control, or when the disease has regressed partially or completely. Further, it is noted that the clinician or treating physician will know how and when to interrupt, adjust, or terminate use of the arsenic trioxide composition as a medication in conjunction with individual patient response.

The effect of the lyophilized composition comprising arsenic of the invention on development and progression of hematological malignancies can be monitored by any methods known to one skilled in the art, including but not limited to measuring: a) changes in the size and morphology of the tumor using imaging techniques such as a computed tomographic (CT) scan or a sonogram; and b) changes in levels of biological markers of risk for hematological malignancies.

In certain embodiments, toxicity and efficacy of the prophylactic and/or therapeutic protocols of the instant invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

In other embodiments, the data obtained from the cell culture assays and animal studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the therapies used in accordance with the present invention also can be determined by using various experimental animal models for the study of cancer such as the scid mouse model or transgenic mice. The following are some assays provided as examples and not by limitation.

The lyophilized composition comprising arsenic of the present invention is prepared as described below in the description and the experimental section. Arsenic or one or more of its chemical forms is the active ingredient, and can optionally contain a pharmaceutically acceptable carrier or excipient, and/or other ingredients provided that these ingredients do not compromise (e.g., reduce) the efficacy lyophilized composition comprising arsenic. Other ingredients that can be incorporated into lyophilized composition comprising arsenic of the present invention, may include, but are not limited to, herbs (including traditional Chinese medicine products), herbal extracts, vitamins, amino acids, metal salts, metal chelates, coloring agents, flavor enhancers, preservatives, and the like.

Any dosage form may be employed for providing the subject with an effective dosage of the oral composition. Dosage forms include tablets, capsules, dispersions, suspensions, solutions, and the like. In one embodiment, compositions of the present invention suitable for oral administration may be presented as discrete units such as capsules, blisters, cachets, or tablets, each containing a predetermined amount of activated and conditioned yeast cells, as a powder or granules or as a solution or a suspension in an aqueous liquid, a non-aqueous liquid, an oil-in-water emulsion, or a water-in-oil liquid emulsion. In preferred embodiments, the oral composition is in the form of a lyophilized powdery or fluffy solid. In general, the compositions are prepared by uniformly and intimately admixing the active ingredient with liquid carriers or finely divided solid carriers or both, and then, if necessary, shaping the product into the desired presentation. Such products can be used as pharmaceuticals or dietary supplements, depending on the dosage and circumstances of its use.

The oral compositions of the present invention may additionally include binding agents (e.g., pregelatinized maize starch, polyvinylpyrrolidone or hydroxypropyl methylcellulose); binders or fillers (e.g., lactose, pentosan, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets or capsules can be coated by methods well known in the art.

In certain embodiments, lyophilized composition comprising arsenic comprises about 0.1, 0.2, 0.3, 0.4, 0.5, 1, 2, 3, 4, 5, 6, 7, 8, 9, 10, 11, 12, 13, 14, 15, 16, 17, 18, 19, 20 21, 22, 23, 24, or 25 mg of the equivalent of arsenic trioxide per ml.

Generally, because of their ease of administration, tablets and capsules represent the most advantageous oral dosage unit form, in which case solid pharmaceutical carriers as described above are employed. In a preferred embodiment, the composition is a capsule. The capsules can be formulated by any commercially available methods. In certain embodiments, the composition is a capsule containing 0.25 mg, 0.5 mg, 1 mg, 2 mg, 3, mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 24 mg, 45 mg, 46 mg, 47 mg, 48 mg, 49 mg, or 50 mg of the lyophilized composition comprising arsenic in powder form.

Additional examples of anti-cancer agents that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2); interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitaminutes D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine octfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

Formulations

In a preferred embodiment, this invention relates to a method for preparing lyophilized composition comprising arsenic, alternatively addressed herein as lyophilized arsenic trioxide ($As_2O_3$), said method comprising:

a. solubilizing $As_2O_3$ powder in water in a vessel, said solubilizing comprising, in the following order:
    i. adding an alkalizing agent to said vessel to a pH of about 12 or higher,
    ii. adding an acid to said vessel to adjust the pH to about 7 to about 8,
    iii. adding a surfactant to said vessel, and
    iv. adding water to said vessel to generate an $As_2O_3$ solution; and
  b. lyophilizing said $As_2O_3$ solution.

In one embodiment of the above method, the alkalizing agent comprises sodium hydroxide (NaOH) or sodium carbonate ($Na_2CO_3$). In another embodiment, the amount of said alkalizing agent added is about 10% to about 100% the amount of the $As_2O_3$ powder. Stated another way, the amount of said alkalizing agent added is about 10, 11, 12, 13, 14, 15, 16, 17, 18, 19, 20, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 96, 97, 98, 99, and 100% the amount of the $As_2O_3$ powder. In another embodiment, the amount of said alkalizing agent added is any number within a range defined by and inclusive of any two numbers stated above.

In yet another embodiment, said acid comprises hydrochloric acid (HCl). In one embodiment, said HCl is about 6M HCl. In one embodiment, the acid is added to said vessel to adjust the pH to about 7.2. In one embodiment, the water is added to said vessel after step a)i), a)ii), a)iii), and/or a)iv).

In one embodiment of the invention, the surfactant comprises sodium lauryl sulfate; Tween 80; betacyclodextrin; poloxamer; tocopheryl polyethylene glycol succinate (TPGS). In one embodiment of the invention, the surfactant is added to about 0.5% v/v to about 4.0% v/v, but does not exceed about 50% $As_2O_3$ concentration.

In one embodiment of the invention, the step of lyophilizing comprises freezing said $As_2O_3$ solution to generate a frozen $As_2O_3$ product and drying said frozen $As_2O_3$ product to generate said lyophilized $As_2O_3$ or the lyophilized composition comprising arsenic. In another embodiment, the freezing step comprises freezing said $As_2O_3$ solution at about −40° C. In another embodiment, the $As_2O_3$ solution is frozen at about −40° C. for at least about 6 hours. In one embodiment, the drying step comprises applying heat and a vacuum to said $As_2O_3$ solid. For example, the drying step comprises heating said $As_2O_3$ product at about −30° C. and about 800 millitorrs for about 60 minutes; heating said $As_2O_3$ product at −20° C. and 500 millitorrs for about 120 minutes; heating said $As_2O_3$ product at about −5° C. and about 500 millitorrs for about 120 minutes; heating said $As_2O_3$ product at about 10° C. and about 500 millitorrs for about 60 minutes; heating said $As_2O_3$ product at about 25° C. and about 500 millitorrs for about 180 minutes.

In another embodiment, said drying step comprises heating said $As_2O_3$ product to about −30° C. and about 800 millitorrs over about 60 minutes and holding at about −30° C. and about 800 millitorrs for about 60 minutes; heating said $As_2O_3$ product to about −20° C. and about 500 millitorrs over about 60 minutes and holding at about −20° C. and about 500 millitorrs for about 120 minutes; heating said $As_2O_3$ product to about −5° C. and about 500 millitorrs over about 300 minutes and holding at about −5° C. and about 500 millitorrs for about 120 minutes; heating said $As_2O_3$ product to about 10° C. and about 500 millitorrs over about 120 minutes and holding at about 10° C. and about 500 millitorrs for about 60 minutes; and heating said $As_2O_3$ product to about 25° C. and about 500 millitorrs over about 60 minutes and holding at about 25° C. and about 500 millitorrs for about 180 minutes.

In one embodiment, the drying step further comprises, following said heating of said $As_2O_3$ product at about 25° C. and about 500 millitorrs for about 180 minutes, heating said $As_2O_3$ product at about 25° C. and about 500 millitorrs for about 120 minutes.

This invention also relates to a method for preparing an oral formulation comprising LCCA, said method comprising:

c. solubilizing $As_2O_3$ powder in water in a vessel, said solubilizing comprising, in the following order:
    i. adding an alkalizing agent to said vessel to a pH of about 12 or higher,
    ii. adding an acid to said vessel to adjust the pH to about 7 to about 8,
    iii. adding a surfactant to said vessel, and
    iv. and adding water to said vessel to generate an $As_2O_3$ solution; and
  d. lyophilizing said $As_2O_3$ solution to generate a lyopremix;
  e. sifting said lyopremix to generate the LCCA powder;
  f. adding a bulking agent to said LCCA powder;
  g. adding one or more lubricants to said LCCA powder to generate said oral formulation comprising LCCA.

In one embodiment of the above method, the alkalizing agent comprises sodium hydroxide (NaOH) or sodium carbonate ($Na_2CO_3$). In another embodiment, the amount of said alkalizing agent added is about 10% to about 100% the amount of the $As_2O_3$ powder. In yet another embodiment, said acid comprises hydrochloric acid (HCl). In one embodiment, said HCl is about 6M HCl. In one embodiment, the acid is added to said the vessel to adjust the pH to about 7.2. In one embodiment, the water is added to said vessel after step c)i), c)ii), c)iii), and/or c)iv).

In one embodiment of the invention, the surfactant comprises sodium lauryl sulfate; Tween 80; betacyclodextrin; poloxamer; tocopheryl polyethylene glycol succinate (TPGS). In one embodiment of the invention, the surfactant is added to about 0.5% v/v to about 4.0% v/v, but does not exceed about 50% $As_2O_3$ concentration.

In one embodiment of the invention, the step of lyophilizing comprises freezing said $As_2O_3$ solution to generate a frozen $As_2O_3$ product and drying said frozen $As_2O_3$ product to generate said lyophilized $As_2O_3$. In another embodiment, the freezing step comprises freezing said $As_2O_3$ solution at about −40° C. In another embodiment, the $As_2O_3$ solution is frozen at about −40° C. for at least about 6 hours. In one embodiment, the drying step comprises applying heat and a vacuum to said $As_2O_3$ product solid. For example, the drying step comprises heating said $As_2O_3$ product at about −30° C.

and about 800 millitorrs for about 60 minutes; heating said As$_2$O$_3$ product at −20° C. and 500 millitorrs for about 120 minutes; heating said As$_2$O$_3$ product at about −5° C. and about 500 millitorrs for about 120 minutes; heating said As$_2$O$_3$ product at about 10° C. and about 500 millitorrs for about 60 minutes; heating said As$_2$O$_3$ product at about 25° C. and about 500 millitorrs for about 180 minutes.

In another embodiment, said drying step comprises heating said As$_2$O$_3$ product to about −30° C. and about 800 millitorrs over about 60 minutes and holding at about −30° C. and about 800 millitorrs for about 60 minutes; heating said As$_2$O$_3$ product to about −20° C. and about 500 millitorrs over about 60 minutes and holding at about −20° C. and about 500 millitorrs for about 120 minutes; heating said As$_2$O$_3$ product to about −5° C. and about 500 millitorrs over about 300 minutes and holding at about −5° C. and about 500 millitorrs for about 120 minutes; heating said As$_2$O$_3$ product to about 10° C. and about 500 millitorrs over about 120 minutes and holding at about 10° C. and about 500 millitorrs for about 60 minutes; and heating said As$_2$O$_3$ product to about 25° C. and about 500 millitorrs over about 60 minutes and holding at about 25° C. and about 500 millitorrs for about 180 minutes.

In one embodiment, the drying step further comprises, following said heating of said As$_2$O$_3$ product at about 25° C. and about 500 millitorrs for about 180 minutes, heating said As$_2$O$_3$ product at about 25° C. and about 500 millitorrs for about 120 minutes.

In one embodiment of the above invention, the bulking agent comprises mannitol. In another embodiment, the one or more lubricants comprises talc and/or magnesium stearate.

In a further step, the above invention comprises filling a capsule with said oral formulation.

This invention also relates to a pharmaceutical composition in a solid dosage form suitable for oral administration, the composition comprising lyophilized arsenic trioxide also known as lyophilized composition comprising arsenic, at least one bulking agent, and at least one lubricant.

In one embodiment, the pharmaceutical composition above is produced by a method comprising:
  h. solubilizing As$_2$O$_3$ powder in water in a vessel, said solubilizing comprising, in the following order:
    v. adding an alkalizing agent to said vessel to a pH of about 12 or higher,
    vi. adding an acid to said vessel to adjust the pH to about 7 to about 8,
    vii. adding a surfactant to said vessel, and
    viii. and adding water to said vessel to generate an As$_2$O$_3$ solution; and
  i. lyophilizing said As$_2$O$_3$ solution to generate a lyopremix;
  j. sifting said lyopremix to generate the LCCA powder;
  k. adding a bulking agent to said LCCA powder;
  l. adding one or more lubricants to said LCCA powder to generate said oral formulation of As$_2$O$_3$.

In one embodiment, the lyopremix or the LCCA has an average particle size distribution D(90) of from about 2 microns to 10 microns. Stated another way, the particle size distribution D(90) of the lyopremix as measured in microns is 2, 3, 4, 5, 6, 7, 8, 9, and 10 microns or a number within a range by defined by any two number thereof.

In one embodiment, the lyopremix or the LCCA has an average particle size distribution D(10) of from about 0.2 microns to 3 microns. Stated another way, the particle size distribution D(10) of the lyopremix as measured in microns is 0.2, 0.3, 0.4, 0.5, 0.6, 0.7, 0.9, 1.0, 1.1, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0 microns or a number within a range by defined by any two number thereof.

In one embodiment, the lyopremix or the LCCA has an average particle size distribution D(50) of from about 0.5 microns to 4 microns. Stated another way, the particle size distribution D(50) of the lyopremix as measured in microns is 0.5, 0.6, 0.7, 0.9, 1.0, 1.1, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0 microns or a number within a range by defined by any two number thereof.

In one embodiment, the lyopremix or the LCCA has a particle size D(90) that is from 10 times smaller than the API and up to 50 times smaller than the API. Stated another way, the D(90) of the lyopremix is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 times smaller than the D(90) of the API.

In one embodiment, the lyopremix or the LCCA surface area is in the range from about from about 0.5 m2/g to about 5 m2/g. In other words, the surface area can be 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0, m2/g, or a number within a range defined by any two numbers herein.

In one embodiment, the lyopremix's or the LCCA's surface area is from 2 times to 80 times more than the surface area of the API powder as measured by the BET method. Stated another way, the BET surface area of the lyopremix is 2, 3, 4, 5, 6, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, and 80 times the surface area of the API powder.

In one embodiment the lyopremix or the LCCA is soluble in cold water. In another embodiment, the lyopremix or the LCCA is from about 2× to about 30× more soluble in cold water (room temperature) than the API powder. Stated another way, the lyopremix or the LCCA is from about 2, 3, 4, 5, 6, 7, 8, 9, 10, 11, 12, 13, 14, 15, 16, 17, 18, 19, 20, 21, 22, 23, 24, 25, 26, 27, 28, 29, or 30× more soluble in cold water (room temperature) than the API powder. In one embodiment, the lyopremix or the LCCA is soluble in alcohol. In another embodiment, the lyopremix or the LCCA is from about 2× to 30× more soluble in alcohol than the API powder. Stated another way, the lyopremix or the LCCA is from about 2, 3, 4, 5, 6, 7, 8, 9, 10, 11, 12, 13, 14, 15, 16, 17, 18, 19, 20, 21, 22, 23, 24, 25, 26, 27, 28, 29, or 30× more soluble in alcohol than the API powder.

From the scanning electron micrograph, it is observed that the lyopremix or the LCCA particles have porous character, which may contribute to the higher solubility, higher surface area, and the smaller average particle size of the lyopremix.

In one embodiment of the above pharmaceutical composition, the alkalizing agent comprises sodium hydroxide (NaOH) or sodium carbonate (Na$_2$CO$_3$). In another embodiment, the amount of said alkalizing agent added is about 10% to about 100% the amount of the As$_2$O$_3$ powder. In yet another embodiment, said acid comprises hydrochloric acid (HCl). In one embodiment, said HCl is about 6M HCl. In one embodiment, the acid is added to said vessel to adjust the pH to about 7.2. In one embodiment, the water is added to said vessel after step h)i), h)ii), h)iii), and/or h)iv).

In one embodiment of the invention, the surfactant comprises sodium lauryl sulfate; Tween 80; betacyclodextrin;

poloxamer; tocopheryl polyethylene glycol succinate (TPGS). In one embodiment of the invention, the surfactant is added to about 0.5% v/v to about 4.0% v/v, but does not exceed about 50% $As_2O_3$ concentration.

In one embodiment of the invention, the step of lyophilizing comprises freezing said $As_2O_3$ solution to generate a frozen $As_2O_3$ product and drying said frozen $As_2O_3$ product to generate said lyophilized $As_2O_3$. In another embodiment, the freezing step comprises freezing said $As_2O_3$ solution at about −40° C. In another embodiment, the $As_2O_3$ solution is frozen at about −40° C. for at least about 6 hours. In one embodiment, the drying step comprises applying heat and a vacuum to said $As_2O_3$ solid. For example, the drying step comprises heating said $As_2O_3$ product at about −30° C. and about 800 millitorrs for about 60 minutes; heating said $As_2O_3$ product at −20° C. and 500 millitorrs for about 120 minutes; heating said $As_2O_3$ product at about −5° C. and about 500 millitorrs for about 120 minutes; heating said $As_2O_3$ product at about 10° C. and about 500 millitorrs for about 60 minutes; heating said $As_2O_3$ product at about 25° C. and about 500 millitorrs for about 180 minutes. In another embodiment, said drying step comprises heating said $As_2O_3$ product to about −30° C. and about 800 millitorrs over about 60 minutes and holding at about −30° C. and about 800 millitorrs for about 60 minutes; heating said $As_2O_3$ product to about −20° C. and about 500 millitorrs over about 60 minutes and holding at about −20° C. and about 500 millitorrs for about 120 minutes; heating said $As_2O_3$ product to about −5° C. and about 500 millitorrs over about 300 minutes and holding at about −5° C. and about 500 millitorrs for about 120 minutes; heating said $As_2O_3$ product to about 10° C. and about 500 millitorrs over about 120 minutes and holding at about 10° C. and about 500 millitorrs for about 60 minutes; and heating said $As_2O_3$ product to about 25° C. and about 500 millitorrs over about 60 minutes and holding at about 25° C. and about 500 millitorrs for about 180 minutes.

In one embodiment, the drying step further comprises, following said heating of said $As_2O_3$ product at about 25° C. and about 500 millitorrs for about 180 minutes, heating said $As_2O_3$ product at about 25° C. and about 500 millitorrs for about 120 minutes.

In one embodiment of the above invention, the bulking agent comprises mannitol. In another embodiment, the one or more lubricants comprises talc and/or magnesium stearate.

In one embodiment, the pharmaceutical composition above comprises lyophilized arsenic trioxide, mannitol, talc, and magnesium stearate. In another embodiment, the pharmaceutical composition of above is a controlled release oral solid pharmaceutical composition. In another embodiment, the pharmaceutical composition above is encapsulated in a capsule.

In one embodiment, the capsule comprises about 1 mg, 5 mg, 10 mg, and 20 mg of the pharmaceutical composition above.

This invention also relates to a kit comprising the pharmaceutical composition above and instructions for use of the same.

In one embodiment, this invention relates to a method of treating a hematological malignancy in a patient in need thereof, comprising the step of administering to the patient a therapeutically effective amount of the pharmaceutical composition described above.

As a matter of example, said hematological malignancy is acute myeloid leukemia, acute nonlymphocytic leukemia, myeloblastic leukemia, promyelocytic leukemia, myelomonocytic leukemia, monocytic leukemia, erythroleukemia, myelodysplastic syndrome, acute promyelocytic leukemia, chronic lymphocytic leukemia, chronic myeloid leukemia, hairy cell leukemia, polycythemia vera, Hodgkin's lymphoma, non-Hodgkin's lymphoma, myeloma, giant cell myeloma, indolent myeloma, localized myeloma, multiple myeloma, plasma cell myeloma, sclerosing myeloma, solitary myeloma, smoldering multiple myeloma, nonsecretary myeloma, osteosclerotic myeloma, plasma cell leukemia, solitary plasmacytoma, or extramedullary plasmacytoma.

In one embodiment, the hematological malignancy is acute promyelocytic leukemia (APL). In a further embodiment of the invention the APL is newly diagnosed APL, or a relapsed APL or refractory APL.

In one embodiment, the pharmaceutical composition is administered daily. In another embodiment, the pharmaceutical composition is administered daily for 52 weeks/year. In yet another embodiment, the pharmaceutical composition is administered in a single dosage range of about 1 mg to about 50 mg. In another embodiment, the pharmaceutical composition is administered in a single dosage range of about 0.1 mg/kg body weight to about 0.3 mg/kg body weight.

In one embodiment of the invention, the patient was previously treated or is currently being treated with chemotherapy and/or radiation. In another embodiment, the method of treatment further comprises administering one or more chemotherapeutic agents to said patient. The chemotherapeutic agent is administered before, after, or simultaneously with said pharmaceutical composition. This invention also relates to a composition comprising LCCA or lyophilized arsenic trioxide, at least one bulking agent, and at least one lubricant. In one embodiment, the lyophilized arsenic trioxide is produced by a method comprising:

m. solubilizing $As_2O_3$ powder in water in a vessel, said solubilizing comprising, in the following order:

ix. adding an alkalizing agent to said vessel to a pH of about 12 or higher, x. adding an acid to said vessel to adjust the pH to about 7 to about 8, xi. adding a surfactant to said vessel, and xii. and adding water to said vessel to generate an $As_2O_3$ solution; and lyophilizing said $As_2O_3$ solution. In one embodiment, the alkalizing agent comprises sodium hydroxide (NaOH) or sodium carbonate ($Na_2CO_3$). In another embodiment of the invention, the amount of said alkalizing agent added is about 10% to about 100% the amount of the $As_2O_3$. In one embodiment, acid comprises hydrochloric acid (HCl), and preferably about 6M HCl. In another embodiment, the acid is added to said vessel to adjust the pH to about 7.2. In another embodiment, water is added to said vessel after step m)i), m)ii), m)iii), and/or m)iv).

In one embodiment, the surfactant comprises sodium lauryl sulfate; Tween 80; betacyclodextrin; poloxamer; tocopheryl polyethylene glycol succinate (TPGS). The surfactant is added to about 0.5% v/v to about 4.0% v/v, but does not exceed about 50% $As_2O_3$ concentration.

Lyophilization
Freezing Step

In one embodiment, the lyophilizing step comprises freezing said $As_2O_3$ solution to generate a frozen $As_2O_3$ product and drying said frozen $As_2O_3$ product to generate lyophilized $As_2O_3$. In one embodiment, the lyophilizing step comprises freezing said $As_2O_3$ solution to at least one of the temperatures from −50, −49, −48, −47, −46, −45, −44, −43, −42, −41, −40, −39, −38, −37, −36, −35, −34, −33, −32, −31, −30, 29, −28, −27, −26, −25, −24, −23, −22, −21, −20, −19, −18, −17, −16, −15, −14, −13, −12, −11, −10, −09, −08, −07, −06, −05, −04, −03, −02, −01, and 0° C. In another embodiment, the freezing temperature is selected from a range defined by and inclusive of any two numbers above. In another embodiment, the freezing step comprises freezing said $As_2O_3$ solution at about −40° C., for at least 6 hours. The freezing step can have several freezing sub-steps, progressively decreasing the temperature. The freezing step and/or the freezing sub-steps can be from about 5 minutes to about 500 minutes each, that is, including every number in between the range, for example, 6, 7, 8, 9, . . . , 497, 498, 499, and 500 minutes.

Sublimation Step

In one embodiment, the sublimation (primary drying) or the secondary drying takes place at a temperature in the range of −50° C. to 35° C. Stated another way, the sublimation can be effected at the following temperatures: −50, −49, −48, −47, −46, −45, −44, −43, −42, −41, −40, −39, −38, −37, −36, −35, −34, −33, −32, −31, −30, −29, −28, −27, −26, −25, −24, −23, −22, −21, −20, −19, −18, −17, −16, −15, −14, −13, −12, −11, −10, −9, −8, −7, −6, −5, −4, −3, −2, −1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35. In one embodiment, the sublimation temperature can be any temperature within a range defined by and inclusive of any two numbers above. In one embodiment, more than one sublimation temperatures are used.

The secondary drying can be performed at higher temperatures, for example, temperatures between 35° C. and 75° C.

The primary or the secondary drying at different temperatures is done for time in the range of 5 minutes to 500 minutes, that is, including every number in between the range, for example, 6, 7, 8, 9, . . . , 497, 498, 499, and 500 minutes. Secondary drying can for longer times, for example, up to 1000 minutes.

Vacuum Application

Vacuum can be applied simultaneously with drying or independently. Vacuum can be applied as the drying continues from one temperature to a second (higher) temperature, or during holding at one temperature. Vacuum can be applied over multiple steps of drying or only some steps of drying. Vacuum application can be alternated with drying. The vacuum applied during the drying step can be in the range of from about 300 millitorrs to about 1000 millitorrs. In one embodiment, the vacuum is 300, 310, 320, 330, 340, 350, 360, 370, 380, 390, 400, 410, 420, 430, 440, 450, 460, 470, 480, 490, 500, 510, 520, 50, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, and 1000 millitorrs or a vacuum defined by and inclusive of a number within a range defined by any two numbers herein.

The drying step comprises applying heat and a vacuum to said $As_2O_3$ product. In one embodiment, the drying step comprises heating said $As_2O_3$ product at about −30° C. and about 800 millitorrs for about 60 minutes; heating said $As_2O_3$ product at about −20° C. and about 500 millitorrs for about 120 minutes; heating said $As_2O_3$ product at about −5° C. and about 500 millitorrs for about 120 minutes; heating said $As_2O_3$ product at about 10° C. and about 500 millitorrs for about 60 minutes; and heating said $As_2O_3$ product at about 25° C. and about 500 millitorrs for about 180 minutes. In another embodiment, the drying step comprises heating said $As_2O_3$ product to about −30° C. and about 800 millitorrs over about 60 minutes and holding at about −30° C. and about 800 millitorrs for about 60 minutes; heating said $As_2O_3$ product to about −20° C. and about 500 millitorrs over about 60 minutes and holding at about −20° C. and about 500 millitorrs for about 120 minutes; heating said $As_2O_3$ product to about −5° C. and about 500 millitorrs over about 300 minutes and holding at about −5° C. and about 500 millitorrs for about 120 minutes; heating said $As_2O_3$ product to about 10° C. and about 500 millitorrs over about 120 minutes and holding at about 10° C. and about 500 millitorrs for about 60 minutes; and heating said $As_2O_3$ product to about 25° C. and about 500 millitorrs over about 60 minutes and holding at about 25° C. and about 500 millitorrs for about 180 minutes.

In yet another embodiment, following said heating of said $As_2O_3$ product at about 25° C. and about 500 millitorrs for about 180 minutes, heating said $As_2O_3$ product at about 25° C. and about 500 millitorrs for about 120 minutes.

In one embodiment of the composition, the bulking agent comprises mannitol, and the one or more lubricants comprises talc and/or magnesium stearate.

This invention also relates to a composition described above that comprises lyophilized arsenic trioxide, mannitol, talc, and magnesium stearate.

In one embodiment, for the compositions and methods described herein, the LCCA is used in a therapeutically effective amount.

EXPERIMENTAL

The reference product was an injectable $As_2O_3$ available in injection form with the strength of 10 mg/10 mL. The development of test product was provided in solid form for oral use. The test product development was initiated as 1 mg, 5 mg, 10 mg, and 20 mg capsules. Lyophilization technique was chosen to modify the physical and/or chemical characteristics of arsenic trioxide including reducing particle size, increasing surface area, and generating other morphological features that may help its solubility, dissolution of the pharmaceutical formulation, and/or bioavailability. Suitable excipients were selected and concentrations were optimized to achieve smooth lyophilization process yielding improvement in the solubility of arsenic trioxide. The laboratory-scale stability data for 15 days at 40° C./75% RH were found satisfactory.

Reference Product—Injectable Form—Arsenic Trioxide

According to the package insert for the injectable arsenic trioxide, arsenic trioxide causes morphological changes and DNA fragmentation characteristic of apoptosis in NB4 human promyelocytic leukemia cells in vitro. Arsenic trioxide also causes damage or degradation of the fusion protein PML/RAR-alpha.

Arsenic trioxide in solution hydrolyzes to its pharmacologically active species arsenious acid (AsIII). Monomethylarsonic acid (MMAV), and dimethylarsinic acid (DMAV) are the main pentavalent metabolites formed during metabolism, in addition to arsenic acid (Asv) a product of AsIII oxidation.

The pharmacokinetics of arsenical species ([AsIII], [Asv], [MMAV], [DMAV]) were determined in 6 APL patients following once daily doses of 0.15 mg/kg for 5 days per week. Over the total single dose range of 7 to 32 mg (administered as 0.15 mg/kg), systemic exposure (AUC) appears to be linear. Peak plasma concentrations of arsenious acid (AsIII), the primary active arsenical species were reached at the end of infusion (2 hours). Plasma concentration of AsIII declined in a biphasic manner with a mean elimination half-life of 10 to 14 hours and is characterized by an initial rapid distribution phase followed by a slower terminal elimination phase. The daily exposure to Asm (mean AUC0-24) was 194 ng-hr/mL (n=5) on Day 1 of Cycle 1 and 332 ng-hr/mL (n=6) on Day 25 of Cycle 1, which represents an approximate 2-fold accumulation.

The primary pentavalent metabolites, MMAV and DMAV, are slow to appear in plasma (approximately 10-24 hours after first administration of arsenic trioxide), but, due to their longer half-life, accumulate more upon multiple dosing than does AsIII. The mean estimated terminal elimination half-lives of the metabolites MMAV and DMAV are 32 hours and 72 hours, respectively. Approximate accumulation ranged from 1.4- to 8-fold following multiple dosing as compared to single dose administration. Asv is present in plasma only at relatively low levels.

Distribution

The volume of distribution (Vss) for AsIII is large (mean 562 L, N=10) indicating that $As^{III}$ is widely distributed throughout body tissues. Vss is also dependent on body weight and increases as body weight increases.

Metabolism

Much of the $As^{III}$ is distributed to the tissues where it is methylated to the less cytotoxic metabolites, monomethylarsonic acid ($MMA^V$) and dimethylarsinic acid ($DMA^V$) by methyltransferases primarily in the liver. The metabolism of arsenic trioxide also involves oxidation of $As^{III}$ to $As^v$, which may occur in numerous tissues via enzymatic or nonenzymatic processes. $As^v$ is present in plasma only at relatively low levels following administration of arsenic trioxide.

Excretion

Approximately 15% of the administered arsenic trioxide injection dose is excreted in the urine as unchanged $As^{III}$. The methylated metabolites of $As^{III}$ (MMAV, DMAV) are primarily excreted in the urine. The total clearance of $As^{III}$ is 49 L/h and the renal clearance is 9 L/h. Clearance is not dependent on body weight or dose administered over the range of 7-32 mg.

Developmental $As_2O_3$

The active pharmaceutical ingredient arsenic trioxide for these experiments was purchased from Sigma-Aldrich as white powder, molecular weight of 197.8 g/mole with the general chemical formula of $As_2O_3$.

For the comparative example, injectable form arsenic trioxide was purchased as Arsenox® (Manufactured by Naprod Life sciences private limited for Intas pharma in India). Arsenic trioxide injection is indicated for induction of remission and consolidation in patients with acute promyelocytic leukemia (APL). It comes in an injection vial form with strength of 10 mg/10 mL (1 mg/mL) ampule.

Because the reference product was available in the injection form and development of test product was in solid form for oral use, the reference product was not charged for stability.

No drug excipient study was performed. Solubility studies were conducted as part of development with different surfactants and solvents.

Development of the Formulation Process

Arsenic trioxide, available in injection form, and development grade powder for oral administration were tested. The powder form of $As_2O_3$ was lyophilized to modify the physical and/or chemical characteristics of arsenic trioxide including reducing particle size, increasing surface area, and generating other morphological features that may help in dissolution and/or bioavailability of the arsenic.

Lyophilization, also known as freeze drying involves removing purified water from a liquid, paste, or solid form, using freezing and vacuum evaporation cycles without melting the ice. Water in solid state (ice) exposed to very low pressure such as vacuum sublimates or passes directly from the solid to the gaseous state. Purified water vapor (or other solvent) leaves the capture by freezing with a condenser or cold trap. This technique retains the volume, appearance and properties of the treated product.

Generally, lyophilization cycle comprises the following steps:
1. Freezing: The product is frozen. This provides a necessary condition for low temperature drying.
2. Vacuum: After freezing, the product is placed under vacuum or low pressure. This enables the frozen solvent in the product to vaporize without passing through the liquid phase, a process known as sublimation.
3. Heat: Heat is applied to the frozen product to accelerate sublimation.
4. Condensation: Low-temperature condensation removes the vaporized solvent from the vacuum chamber by converting it back to a solid. This completes the separation process.

The first step in the lyophilization process is to freeze a product to solidify all of its purified water molecules. Once frozen, the product is placed in a vacuum and gradually heated without melting the product. This process, called sublimation, transforms the ice directly into purified water vapor, without first passing through the liquid state. The purified water vapor given off by the product in the sublimation phase condenses as ice on a collection trap, known as a condenser, within the lyophilizer's vacuum chamber.

Lyophilization has many advantages compared to other drying and preserving techniques. For example, lyophilization maintains the quality of the food/biochemical and chemical reagents because they remain at temperatures below the freezing-point during the process of sublimation. Lyophilization is particularly important when processing lactic bacteria, because these products are easily affected by heat. Food/biochemicals and chemical reagents which are lyophilized can usually be stored without refrigeration, which results in a significant reduction of storage and transportation costs. Lyophilization greatly reduces weight, and this makes the products easier to transport. For example, many foods contain as much as 90% purified water. These foods are ten times lighter after lyophilization. Because they are porous, most freeze-dried products can be easily rehydrated. Lyophilization does not significantly reduce volume; therefore purified water quickly regains its place in the molecular structure of the food/biochemicals and chemical reagents.

Based on literature and process (different solubility enhancers like sodium lauryl sulfate, Tween 80®, Poloxamer and pH adjusting agents such as sodium hydroxide, sodium carbonate, sodium alginate, and hydrochloric acid to improve the solubility were selected for initial development. The dissolution medium used was 0.1N HCl, 900 ml, paddle (mixing) at 100 rpm for initial developmental activity. Reference product is available in single strength (10 mg/10 mL) and the test product was initiated for different strengths for oral administration with dose weight proportionality. As reference product was available in 10 mg strength, the formulation development was initiated with 10 mg strength.

Experiment No. L040/1/001

The objective of this experiment was to perform solubility study for arsenic trioxide, using sodium hydroxide as pH adjusting agent, surfactants namely sodium lauryl sulfate and Tween 80®, and different solvents such as isopropyl alcohol and ethanol.

In the first step, 4 g of arsenic trioxide was added to 600 mL of purified water under stirring conditions in a container. Next, about 35 mL of 3M NaOH (12 g of NaOH dissolved in 100 mL of purified water) was added, drop-wise, under magnetic stirring at 1000 rpm for 15 to 30 minutes, until a clear solution was formed. To this solution, 1 L purified water added. The pH was measured to be 12.7 units. It was adjusted with a target of 7 to 8 units, using about 16.5 mL of 6M HCl (105.6 mL added to 200 mL of purified water). A pH of about 7.2 was observed. This solution was made up to 2 L with addition of purified water. The pH remained unchanged at 7.3.

TABLE 1

| No. | Ingredients | L040/1/001A mg/unit | L040/1/001A quantity/batch |
|---|---|---|---|
| 1. | Arsenic trioxide | 10 | 4 g |
| 2. | 3M NaOH | 10.5 | 35 mL |
| 3. | 6M HCl | Qs* | 16.5 mL |
| 4. | Purified water | Qs* | Up to 2000 mL |

*Qs—Quantity sufficient

Experiment No. L040/1/001B

The objective of this experiment was to perform solubility study for arsenic trioxide with sodium lauryl sulfate. In the first step, 50 g of purified water was taken in glass beaker, to which 0.5 g of sodium lauryl sulfate was added under stirring until a clear solution was formed. Next, 5 g of $As_2O_3$ was added under stirring to this solution. The $As_2O_3$ did not dissolve in the solution even after a 30-minutes stirring. In the next step, 30 g of purified water was added to determine if the $As_2O_3$ would solubilize. No solubility was observed. Even after a further addition of 2 g sodium lauryl sulfate, no solubility was observed after 30 minutes of stirring. Two batches were prepared: L040/1/001B1 and L040/1/001B2. The data are reported in Table 2 below.

TABLE 2

| No. | Ingredients | L040/1/001B1 mg/unit | L040/1/001B1 quantity/batch (g) | L040/1/001B2 mg/unit | L040/1/001B2 quantity/batch (g) |
|---|---|---|---|---|---|
| 1. | Arsenic trioxide | 10 | 5 | 10 | 5 |
| 2. | Sodium lauryl sulfate | 1 | 0.5 | 5 | 2.5 |
| 3. | Purified water | Qs | 80 | Qs | 80 |

*Qs—Quantity sufficient

Experiment No. L040/1/001D

The objective of this experiment was to perform solubility enhancement for arsenic trioxide with cyclodextrin (kleptose). In the first step, 50 g of purified water was taken in glass beaker, to which, 0.5 g of cyclodextrin was added with stirring until clear a solution was formed. To the above solution, 5 g of $As_2O_3$ drug was added. Even after 30 minutes of stirring, $As_2O_3$ did not dissolve in the solution. Into this solution, another 30 g of purified water was added. The $As_2O_3$ drug did not dissolve. The $As_2O_3$ drug did not dissolve even after a further 2-g addition of cyclodextrin followed by a 30-minutes stirring. Table 3 summarizes the data for this experiment.

TABLE 3

| No. | Ingredients | L040/1/001D1 mg/unit | L040/1/001D1 quantity/batch (g) | L040/1/001D2 mg/unit | L040/1/001D2 quantity/batch (g) |
|---|---|---|---|---|---|
| 1. | Arsenic trioxide | 10 | 5 | 10 | 5 |
| 2. | Cyclodextrin | 1 | 0.5 | 5 | 2.5 |
| 3. | Purified water | Qs | 80 | Qs | 80 |

*Qs—Quantity sufficient

Experiment No. L040/1/001E

The objective of this experiment was to perform solubility enhancement for arsenic trioxide with Tween 80®. In the first step, 50 g of purified water was taken in a glass beaker, to which 0.5 g of Tween 80® was added under stirring until clear solution was formed. To this solution, 5 g of $As_2O_3$ drug was added under stirring. The $As_2O_3$ remained insoluble even after 30 minutes of stirring. To this solution, another 30 g of purified water added, but the $As_2O_3$ remained insoluble. Even a further addition of 2 g of Tween 80® to the solution failed to dissolve the $As_2O_3$ even after 30 minutes of stirring.

TABLE 4

| No. | Ingredients | L040/1/001E1 mg/unit | L040/1/001E1 quantity/batch (g) | L040/1/001E2 mg/unit | L040/1/001E2 quantity/batch (g) |
|---|---|---|---|---|---|
| 1. | Arsenic trioxide | 10 | 5 | 10 | 5 |
| 2. | Tween 80 ® | 1 | 0.5 | 5 | 2.5 |
| 3. | Purified water | Qs | 80 | Qs | 80 |

*Qs—Quantity sufficient

Experiment No. L040/1/001F

The objective of these experiments was to use various solvents for the solubility study of $As_2O_3$.

Isopropyl Alcohol

In a beaker, 1.5 g of $As_2O_3$ drug was added to 50 mL isopropyl alcohol. The $As_2O_3$ did not dissolve even after 30 minutes stirring. The drug did not dissolve even after an additional 30 mL addition of isopropyl alcohol ad 30 minutes of stirring.

Ethanol

In a beaker, 1.5 g of $As_2O_3$ drug was added to 50 mL ethanol. The drug was insoluble after 30 minutes of stirring. The drug did not dissolve even after an additional 30 mL of ethanol was added accompanied by 30 minutes of stirring.

Thus, from the above series of experiments, it was observed that only the L040/1/001A composition formed clear solution.

Experiment No. L040/1/002

The objective of this experiment was to evaluate the exact quantity of sodium hydroxide required to dissolve the arsenic trioxide and to evaluate the effect of pH on solubility of arsenic trioxide using different excipients.

Experiment No. L040/1/002A—NaOH Quantity to Solubilize the Arsenic Trioxide

In a glass beaker, 30 mL of purified water was added, and its pH was measured at 6.7 units to 7.0 units. To this solution, 200 mg $As_2O_3$ drug was added with stirring. The pH was observed around 5.6. $As_2O_3$ particles were observed as floating in the solution. Into this solution was added, in drop-wise fashion, a 1N NaOH solution (4 g of sodium hydroxide pellets dissolved in 100 mL of purified water). The drug remained insoluble even after addition of 0.6 mL of 1N NaOH and 10 minutes of stirring. The pH was measured around 9.21. A further amount of 1.4 mL of 1N NaOH was added under stirring. The drug was still insoluble, with a pH of 12.21. Upon a subsequent addition of 1.6 mL of NaOH, with stirring, the drug was observed to dissolve at a pH of 12.37. Into this solution was added an extra 200 mg of $As_2O_3$ drug, which was not found to dissolve in the solution (the pH was found to be 12.27). A 2-mL addition of 1N NaOH was undertaken with stirring and the drug was found to dissolve at a pH of 12.33. A further 600 mg addition of the drug to the solution showed the drug to be insoluble at a pH of 12.27. However, when 1N NaOH was added gradually (6.9 mL) the drug was found to dissolve at a pH 12.39. Thus, 5 mg of sodium hydroxide required to dissolve the 10 mg of arsenic trioxide by keeping 30 ml of purified water as constant.

TABLE 5

| Ingredients | Quantity | mg/unit |
| --- | --- | --- |
| Arsenic trioxide | 1000 mg | 10 mg |
| NaOH | 12.5 mL (500 mg of NaOH) | 5 mg |
| Purified water | 30 mL | Qs* |

*Qs—Quantity sufficient

Experiment No. L040/1/002B

The objective of this experiment was to evaluate the pH dependent solubility of arsenic trioxide using L-arginine (pH approx. 4). In a beaker 200 mg of L-arginine was dissolved in 100 mL of purified water (2 mg/mL solution) under continuous stirring. From this solution 50 mL was used to dissolve 50 mg of the $As_2O_3$ drug. However, no dissolution was observed; the pH was noted to be 4.94.

TABLE 6

| Ingredients | Quantity | mg/unit |
| --- | --- | --- |
| Arsenic trioxide | 50 mg | 10 mg |
| L-Arginine | 100 mg | 20 mg |
| Purified water | 50 mL | Qs* |

*Qs—Quantity sufficient

Experiment No. L040/1/002D

The objective of this experiment was to evaluate the pH dependent solubility of arsenic trioxide using sodium bicarbonate (pH approx. of 8). In a beaker 200 mg of sodium bicarbonate was dissolved in 100 mL of purified water (2 mg/mL solution). From this solution, 50 mL was taken (pH of 8.2) and 50 mg of $As_2O_3$ drug was added to it. No solubility was observed (at a pH of 8.0).

TABLE 7

| Ingredients | Quantity | mg/unit |
| --- | --- | --- |
| Arsenic trioxide | 50 mg | 10 mg |
| Sodium bicarbonate | 100 mg | 20 mg |
| Purified water | 50 mL | Qs* |

*Qs—Quantity sufficient

Experiment No. L040/1/002E

The objective of this experiment was to evaluate the pH dependent solubility of arsenic trioxide using L-arginine base (pH approx. of 12). In a beaker, 200 mg of L-arginine base was dissolved in 100 mL of purified water (2 mg/mL solution) under continuous stirring. From this solution, 50 mL was used to dissolve 50 mg of the $As_2O_3$ drug (pH of 10.90). However, no dissolution was observed; the pH was noted to be 10.53.

TABLE 7.1

| Ingredients | Quantity | mg/unit |
| --- | --- | --- |
| Arsenic trioxide | 50 mg | 10 mg |
| L-Arginine | 100 mg | 20 mg |
| Purified water | 50 mL | Qs* |

*Qs—Quantity sufficient

Experiment No. L040/1/002F

The objective of this experiment was to evaluate the pH dependent solubility of arsenic trioxide using sodium carbonate (pH approx. of 12). In a beaker 50 mg of sodium carbonate was added to 50 mL of purified water (1 mg/mL solution). To this solution, 50 mg of $As_2O_3$ drug was added to it under stirring at a pH of 11.25. No solubility of the drug was observed. However, when the concentration of sodium carbonate was gradually increased up to 50 mg of sodium carbonate/mL, the arsenic trioxide was found to be soluble in the solution at a pH of 11.46.

TABLE 8

| Ingredients | Quantity | mg/unit |
| --- | --- | --- |
| Arsenic trioxide | 50 mg | 10 mg |
| Sodium carbonate | 2500 mg | 500 mg |
| Purified water | 50 mL | Qs* |

*Qs—Quantity sufficient

Thus, overall, the drug was insoluble in entire pH range from 4 to 12 when using arginine, arginine base, or sodium bicarbonate, but was found to be soluble using sodium carbonate with higher concentration (500 mg of sodium carbonate was required for dissolving 10 mg of arsenic trioxide).

Experiment No. L040/1/002G

The objective of this experiment was to repeat the experiment of L040/1/002A but with bulking agents such as lactose monohydrate and mannitol for subsequent lyophilization. In the first step, 10 g of arsenic trioxide drug was added to 300 mL purified water under stirring, and then, 125 mL of 1N NaOH added under stirring. The drug was found to be soluble. This solution was divided into two equal parts:

L040/1/002G1: In the first part, lactose monohydrate was added (3.5 g) under stirring and the solution kept aside for physical observation and then for lyophilization (pH 12.34). After around 24 hours at room temperature, the clear solution turned brown and after 36 hours, the intensity of color increased and turned dark brown, and thus, lyophilization was not carried out.

L040/1/002G2: For the second part, mannitol (3.5 g) was added under stirring and the solution was kept aside for physical observation and subsequent lyophilization (pH 12.64). After around 24 hours, the solution did not change physically, and the clear solution was charged for lyophilization for 24 hours. After lyophilization, the material looked very sticky in nature and it was very difficult to fill into capsules. It is possible that the stickiness was a result of the corrosive nature of NaOH, or due to a high pH of solution (12.5), or simply due to the presence of mannitol.

TABLE 8.1

| Ingredients | Quantity (L040/1/002G) | mg/unit |
|---|---|---|
| Arsenic trioxide | 10 mg | 10 mg |
| NaOH | 125 mL | 5 mg |
| Purified water | 300 mL | Qs* |
| Total solution | 425 mL | |

*Qs—Quantity sufficient

TABLE 8.2

| Ingredients | L040/1/002G1 | L040/1/002G2 |
|---|---|---|
| Solution (L040/1/002G) | 212.5 mL | 212.5 mL |
| Lactose monohydrate (Pharmatose 200M) | 3.5 g | — |
| Mannitol (Pearlitol SD 200) | — | 3.5 g |

*Qs—Quantity sufficient

In the next step, other surfactants were evaluated as solubilizing agents for arsenic trioxide. Also, one additional experiment was performed with sodium carbonate with increased quantity of purified water instead of NaOH. One further experiment also was performed using NaOH with pH adjustment between 7 and 8. Another experiment was performed to evaluate the effect of mannitol on sticky nature after lyophilization.

Experiment No. L040/1/003

The objective of this experiment was to perform the solubility of arsenic trioxide using Poloxamer and sodium carbonate.

L040/1/003A: Solubility Enhancement Using Poloxamer

In a beaker, 200 mg of Poloxamer was dissolved in 100 mL of purified water (2 mg/mL solution) under stirring. From this solution, 50 mL was taken and 50 mg of drug was added. The drug was found to be insoluble. A further addition of 50 mg of Poloxamer did not dissolve the drug either even after a 20-minute stirring step.

TABLE 9

| Ingredients | Quantity (L040/1/003A) | mg/unit |
|---|---|---|
| Arsenic trioxide | 50 mg | 10 mg |
| Poloxamer 188 | 150 mg | 30 mg |
| Purified water | 50 mL | Qs* |

*Qs—Quantity sufficient

L040/1/003B: Solubility Enhancement with Increased Quantity of Purified Water

This experiment was similar to L040/1/002F. In a beaker 1250 mg of sodium carbonate was added to 50 ml (25 mg of sodium carbonate/ml) of purified water. To this solution, 50 mg of arsenic trioxide drug was added under stirring, but no solubility of the drug was observed (pH of 11.25). Adding 100 mL of purified water did not dissolve the drug either.

TABLE 10

| Ingredients | Quantity (L040/1/003B) | mg/unit |
|---|---|---|
| Arsenic trioxide | 50 mg | 10 mg |
| Sodium Carbonate | 1250 mg | 250 mg |
| Purified water | 150 mL | Qs* |

*Qs—Quantity sufficient

Experiment L040/1/004

The objective of this experiment was to take the trial using sodium hydroxide and bulking agent (mannitol) and to evaluate the effect of the sticky nature by adjusting the pH around 8 (using 6M hydrochloric acid) after lyophilization. Arsenic trioxide was dispersed in purified water and 12 mL of 3M NaOH was added under stirring, until clear solution formed. The pH was adjusted using 6M HCl to between 7 and 8. Purified water was added up to 500 ml to the above solution and it was divided into two lots:

Lot 1: L040/1/004A1: 250 mL loaded for lyophilization for 24 hours.

Lot 2: L040/1/004A2: 250 mL, mannitol added under stirring and loaded for lyophilization for 24 hours.

TABLE 11

| Ingredients | mg/unit | Batch (100 Capsules) |
|---|---|---|
| Arsenic trioxide | 10 mg | 1 gm |
| NaOH | 14.4 mg | 12 mL (1.44 g) |
| 6M HCl | Qs* | Qs* |
| Purified water | Qs* | 500 mL |

*Qs—Quantity sufficient

TABLE 11.1

| | L040/1/004A1 mg/unit | L040/1/004A1 g | L040/1/004A2 mg/unit | L040/1/004A2 G |
|---|---|---|---|---|
| Drug Solution | | 250 mL | | 250 mL |
| Pearlitol 100SD (mannitol) | | | 20 | 1 |
| Weight | 24.4 | 1.22 | 44.4 | 2.22 |

Experiment L040/1/004B

The objective of this experiment was to prepare the lyopremix for lyophilization. The trial was taken using sodium hydroxide in solid form with decreased purified water quantity and using mannitol as bulking agent. In the first step, arsenic trioxide and NaOH were dispersed in purified water and stirring was continued until a clear solution was formed. To this solution, 6M HCl was added and it was charged for lyophilization for 24 hours. After a 24-hour lyophilization, for the L040/1/004A1 batch, white fluffy powder was observed. For the L040/1/004A2, an off-white color, sticky material was observed, which was critical to remove from the petridish. For the L040/1/004B, a white fluffy powder was observed. It was concluded based on these experiments that the sticky nature of the material (lyopremix) is due to the mannitol in the solution.

In the first step, the lyophilized form of arsenic trioxide and NaOH were added to pearlitol SD 200 and sifted through a #40-mesh (400-micron) and blended for 10 min. In the next step, talc and magnesium stearate were sifted through a #60-mesh (250-micron) and added to the material from the first step and blended for 5 min. The final blend was filled into size "0" hard gelatin capsule shells under Laminar Airflow System.

TABLE 12

Composition for Lyopremix

| Ingredients | L040/1/004B mg/unit | L040/1/004B Batch (500 Capsules) Theoretical |
|---|---|---|
| Arsenic trioxide | 10 | 5 g |
| NaOH | 10 | 5 g |
| 6M HCl | Qs* | 18 ml |
| Purified water | Qs* | 80 ml |
| Lyopremix Weight |  | 10 g |

Qs*—Quantity sufficient

The L040/1/004B batch was further processed using mannitol as bulking agent.

TABLE 12.1

Composition for Final Blend

| Ingredients | L040/1/004B mg/unit | L040/1/004B Batch (500 Capsules) Theoretical |
|---|---|---|
| Lyopremix | 20 | 10 |
| Pearlitol SD 200 | 78 | 39 |
| Talc | 1 | 0.5 |
| Mg stearate | 1 | 0.5 |
| Total | 100 |  |

Experiment No. L040/1/005

The objective of this experiment was to evaluate the dissolution of drug, as such arsenic trioxide filled in "0" size hard gelatin capsule shells (which is equivalent to 10 mg). It was found that dissolution was incomplete even at 60 minutes.

TABLE 13

Dissolution and assay comparison of reference and test product
DISSOLUTION (0.1N HCl, 100 rpm, 900 ml, Paddle)

| Time | Reference Product | L040/1/004B | L040/1/005 |
|---|---|---|---|
| 10 min | — | 67.83 | 80.31 |
| 60 min | — | 73.46 | 81.71 |
| Assay | 110% | 94.53 | 99.71 |

The next trials were planned using different surfactants in formulation to improve the dissolution.

In the L040/1/006 experiment, the trial taken was similar to L040/1/004B and based on precipitation of solution, solvent (purified water) quantity was optimized as 25 mg/ml of arsenic trioxide. In the L040/1/007, experiment, the trial taken was with and without inclusion of different surfactants to evaluate the dissolution and Differential Scanning calorimetry (DSC) study. For the arsenic trioxide capsules, the objective was to prepare drug solution (25 mg/mL of arsenic trioxide) with incorporation of different surfactants.

In the first step, arsenic trioxide was dispersed in 64 mL of purified water. In the next step, 4 g of sodium hydroxide was added to above step and solubility of drug was observed at pH of 12.82. To this solution, 6M HCl was added and pH was observed to be 8.05. Into this solution, purified water was added and the solution divided into different parts (each part contained 40 ml):
L040/1/007: 40 ml of drug solution;
L040/1/007A: 0.5 g of sodium lauryl sulfate added to 40 ml of drug solution; and
L040/1/007B: 0.5 g of Tween 80® added to 40 ml of drug solution.

The solutions L040/1/007 and L040/1/007A were analyzed by Differential Scanning calorimetry (DSC) to evaluate the melting point. From the DSC studies, it is clear that there was no significant change in the melting point.

TABLE 14

| Ingredients | Qty/batch |
|---|---|
| Drug | 4 g |
| NaOH | 4 g |
| 6M HCl | 16 ml |
| Purified water | 144 ml |

| Experiment No. | L040/1/007 | L040/1/007A | L040/1/007B |
|---|---|---|---|
| Drug solution | 40 ml | 40 ml | 40 ml |
| Sodium lauryl sulfate |  | 0.5 g |  |
| Tween 80 ® |  |  | 0.5 g |

Experiment L040/1/008

The next experiment's objective was to use sodium lauryl sulfate in two different concentrations for lyophilization in a trial similar to the Experiment L040/1/007. Into a beaker, 160 mL of purified water was taken and to this 10 g of arsenic trioxide and 10 g of NaOH were added and stirring was continued until clear solution was formed (pH 12.38). To this solution, was added 40 mL of 6M HCl under stirring (pH of 8.04). Furthermore, 200 mL of purified water was added to above solution under stirring (pH 8.18). This solution was then divided into different parts (each part contained 80 mL):
Part 1: L040/1/008A: As is solution.
Part 2: L040/1/008E: 1 g of sodium lauryl sulfate was added to 80 ml of solution under stirring (label claim: 25 mg contains 10 mg of arsenic trioxide).
Part 3: L040/1/008F: 0.2 g of sodium lauryl sulfate was added to 80 mL of solution under stirring (label claim: 21 mg contains 10 mg of arsenic trioxide).

Subsequently, all solutions were loaded for lyophilization for 24 hours and samples were collected after lyophilization.

TABLE 15

| | L040/1/008 (qty/batch in g) | | |
|---|---|---|---|
| Ingredients | L040/1/008A | L040/1/008E | L040/1/008F |
| Arsenic trioxide | 10 mL | 10 mL | 10 mL |
| NaOH | 10 mL | 10 mL | 10 mL |
| 6M HCl | 40 mL | 40 mL | 40 mL |
| Purified water | 400 mL | 400 mL | 400 mL |
| Drug solution | 80 mL | 80 mL | 80 mL |
| Sodium lauryl sulfate (SLS) | — | 1.0 | 0.2 |
| Theoretical yield (g) | 4.0 | 5.0 | 4.2 |

TABLE 15.1

| Batch No. | Label claim (Theoretical) | Theoretical Yield (g) | Pract. Yield (g) |
|---|---|---|---|
| L040/1/008A (without surfactant) | 20 mg ≈ 10 mg of Arsenic trioxide | 4.0 | 5.4062 |
| L040/1/008E (SLS) Ratio (Drug:surfact): 2:1 | 25 mg ≈ 10 mg of Arsenic trioxide | 5.0 | 5.7801 |

TABLE 15.1-continued

| Batch No. | Label claim (Theoretical) | Theoretical Yield (g) | Pract. Yield (g) |
|---|---|---|---|
| L040/1/008F (SLS) Ratio (Drug:surfact): 10:1 | 21 mg ≈ 10 mg of Arsenic trioxide | 4.2 | 5.0093 |

The practical yield of each batch was higher than theoretical yield, which was attributed to the moisture uptake by the lyopremix. Based on assay value, the lyopremix was blended with extra-granular material and filled into capsules.

TABLE 16

Assay and moisture content results:

| Batch No. | Label claim (Theoretical) | Moisture content | Assay (%) |
|---|---|---|---|
| L040/1/008A (without surfactant) | 20 mg ≈ 10 mg of Arsenic trioxide | 12.4 | 83.12 |
| L040/1/008E (SLS): 2:1 | 25 mg ≈ 10 mg of Arsenic trioxide | 11.5 | 86.13 |
| L040/1/008F (SLS) 10:1 | 21 mg ≈ 10 mg of Arsenic trioxide | 11.8 | 82.87 |

Based on above assay, the following filling trials were performed.

TABLE 17

Composition for L040/1/009B

| Ingredients | Actual (mg/unit) | Based on Assay fill wt. (mg/unit) | Batch Size (g) |
|---|---|---|---|
| Lyopremix (L040/1/008A) | 20 | 24.060 | 2.165 |
| Mannitol (Pearlitol SD 200) | 78 | 73.940 | 6.655 |
| Talc | 1 | 1.000 | 0.090 |
| Mg stearate | 1 | 1.000 | 0.090 |
| Total | 100 | 100.000 | 9.000 |

TABLE 18

Composition for L040/1/012B

| Ingredients | Actual (mg/unit) | Based on Assay fill wt. (mg/unit) | Batch Size (g) |
|---|---|---|---|
| Lyopremix | 25 | 29.020 | 2.612 |
| Mannitol (Pearlitol SD 200) | 75 | 68.980 | 6.208 |
| Talc | 1 | 1.000 | 0.090 |
| Mg stearate | 1 | 1.000 | 0.090 |
| Total | 102 | 100.000 | 9.000 |

TABLE 19

COMPOSITION FOR L040/1/013B

| Ingredients | Actual (mg/unit) | Based on Assay fill wt (mg/unit) | Batch size (g) |
|---|---|---|---|
| Lyopremix (L040/1/008F) | 21.000 | 25.342 | 2.281 |
| Mannitol (Pearlitol SD 200) | 77.000 | 72.658 | 6.539 |
| Talc | 1.000 | 1.000 | 0.09 |
| Mg stearate | 1.000 | 1.000 | 0.09 |
| Total | 100.000 | 100.000 | — |

The lyophilized form of arsenic trioxide and NaOH (lyopremix) were added to pearlitol SD 200 and sifted through #40-mesh and blended for 10 minutes. Talc and magnesium stearate were sifted through #60-mesh and were added to above material and blended for 5 minutes. This powder was filled into size "2" capsules.

TABLE 20

DISSOLUTION (0.1N HCl, 100 rpm, 900 ml, Paddle)

| Time in Minutes | L040/1/009B | L040/1/012B | L040/1/013B |
|---|---|---|---|
| 15 minutes | 73 | 87 | 88 |
| 60 minutes | 75 | 89 | 90 |

From the above data, it is clear that a complete dissolution was observed in all the batches. In the next step, bigger batch samples, similar to L040/1/012B, and all strengths, 1 mg, 5 mg, 10 mg and 20 mg were filled. Based on the batch no. L040/1/012B, confirmatory batch (batch no. L040/4/014) was manufactured with all the strengths (1 mg, 5 mg, 10 mg, and 20 mg).

TABLE 21

Solution Preparation and Lyophilization

| No. | Name of the Ingredient/ Brand Name | Manufacturer | Specification | Cap. Quant. (mg) | Cap. Quant. (mg) | Cap. Quant. (mg) | Cap. Quant. (mg) |
|---|---|---|---|---|---|---|---|
| 1. | Arsenic trioxide | Sigma-Aldrich | IH | 1 | 5 | 10 | 20 |
| 2. | Sodium hydroxide pellets | J. T. Bakers | USP-NF | 1 | 5 | 10 | 20 |

TABLE 21-continued

Solution Preparation and Lyophilization

| No. | Name of the Ingredient/ Brand Name | Manufacturer | Specification | Cap. Quant. (mg) | Cap. Quant. (mg) | Cap. Quant. (mg) | Cap. Quant. (mg) |
|---|---|---|---|---|---|---|---|
| 3. | 6M Hydrochloric Acid | J. T. Bakers | USP-NF | Qs | Qs | Qs | Qs |
| 4. | Purified water | — | — | Qs | Qs | Qs | Qs |
| 5. | Purified water | — | — | Qs | Qs | Qs | Qs |
| 6. | Sodium lauryl sulfate (Texapan) | Cognis | USP-NF | 0.5 | 2.5 | 5 | 10 |
| | Lyopremix (mg) | | | 2.5 | 12.5 | 25 | 50 |

*Qs—quantity sufficient

TABLE 22

Blending & Lubrication

| No. | Name of the Ingredient/Brand Name | Manufacturer | Specification | Cap. Quant. (mg) | Cap. Quant. (mg) | Cap. Quant. (mg) | Cap. Quant. (mg) |
|---|---|---|---|---|---|---|---|
| 1. | Lyopremix | | IH | 2.5 | 12.5 | 25 | 50 |
| 2. | Mannitol (Pearlitol SD 200) | Roqette | USP-NF | 7.3 | 36.5 | 73 | 146 |
| 3. | Talc (Luzenac) | Luzenac | USP | 0.1 | 0.5 | 1 | 2 |
| 4. | Magnesium stearate (Ligamed MF2V) | Peter Greven | USP-NF | 0.1 | 0.5 | 1 | 2 |
| | Fill Weigh (mg) | | | 10 | 50 | 100 | 200 |

In the next step, arsenic trioxide and sodium hydroxide pellets were dispersed in 480 ml of purified water and stirring was continued until a clear solution was formed. To this solution was added 120 mL of 6M HCl under stirring. Sodium lauryl sulfate, 15 g, was added to this solution under stirring. An additional 20 mL of purified water was added to above solution. This solution was divided into two parts (L040/4/014A and L040/4/014B) and lyophilized for around 30 hours.

TABLE 23

| Batch Numbers | Label claim (Theoretical) | Assay |
|---|---|---|
| #L040/4/014A | 25 mg ≈ 10 mg of Arsenic trioxide | 82.35 |
| #L040/4/014B | 25 mg ≈ 10 mg of Arsenic trioxide | 83.35 |

TABLE 24

| | L040/4/014B1 | | |
|---|---|---|---|
| Ingredients | mg/unit | mg/unit (Based on assay) | Qty/batch (g) |
| Lyopremix (L040/4/014B) | 50 | 59.98 | 53.68 |
| Mannitol (pearlitol SD 200) | 146 | 136.02 | 121.74 |

TABLE 24-continued

| | L040/4/014B1 | | |
|---|---|---|---|
| Ingredients | mg/unit | mg/unit (Based on assay) | Qty/batch (g) |
| Talc | 2 | 2 | 1.79 |
| Magnesium stearate | 2 | 2 | 1.79 |
| Total | 200 | 200 | — |

In the next step, lyophilized form of arsenic trioxide and NaOH (lyopremix) were added to pearlitol SD 200 and sifted through #40-mesh and blended for 10 minutes. Talc and magnesium stearate were sifted through #60-mesh and added to above material and blended for 5 minutes. The final blend and suitable capsules and glass vials were prepared as given below.

TABLE 25

| Strength | Batch No | Batch size | Pack |
|---|---|---|---|
| 20 mg | L040/4/014B1 | 400 units | HDPE |
| 10 mg | L040/3/014B1 | 400 units | HDPE |
| 10 mg lubricated blend | L040/3/014B2 | 350 units | Glass Vial |
| 5 mg | L040/2/014B1 | 400 units | HDPE |
| 1 mg | L040/1/014B1 | 400 units | HDPE |

TABLE 26

| Batch No. | L040/4/014B1 | L040/3/014B1 | L040/3/014B2 | L040/2/014B1 | L040/1/014B1 |
|---|---|---|---|---|---|
| Strength | 20 mg | 10 mg | 10 mg | 5 mg | 1 mg |
| Capsule Size/Vial Filling | 2 | 3 | Glass vial | 5 | 5 |
| Fill Weight (mg) | 200 | 100 | 100 | 50 | 10 |
| Dissolution (0.1N HCl; 100 rpm; 900 mL; Paddle for 15 min. | 86 | 92 | | 77 | 93 |

TABLE 27

Stability Studies-L040/4/014BT (20 mg)
Batch No. L040/4/014B1 (20 mg)

| | Initial | 40 degree C./75% RH (15 days) |
|---|---|---|
| Assay | 95.15 | 101.41 |
| Moisture content | 2.24 | 2.69 |
| Dissolution (0.1N HCl; 100 rpm; 900 mL; Paddle at 15 min.) | 86 | 98 |

TABLE 28

Stability Studies-L040/3/014B1 (10 mg)
Batch No. L040/3/014B1 (10 mg)

| | Initial | 40 degree C./75% RH (15 days) |
|---|---|---|
| Assay | 102.4 | 99.15 |
| Moisture content | 2.38 | 2.19 |
| Dissolution (0.1N HCl; 100 rpm; 900 mL; Paddle at 15 min.) | 92 | 100 |

TABLE 29

Stability Studies-L040/3/014B2 (10 mg lubricated blend)
Batch No. L040/3/014B2 (10 mg lubricated blend)

| | Initial | 40 degree C./75% RH (15 days) |
|---|---|---|
| Assay | 98.2 | 99.78 |
| Moisture content | 1.90 | 2.32 |

TABLE 30

Stability Studies-L040/2/014B1 (5 mg)
Batch No. L040/2/014B1 (5 mg)

| | Initial | 40 degree C./75% RH (15 days) |
|---|---|---|
| Assay | 98.8 | 99.95 |
| Moisture content | 2.63 | 2.82 |
| Dissolution (0.1N HCl; 100 rpm; 900 mL; Paddle at 15 min.) | 77 | 84 |

TABLE 31

Stability Studies-L040/1/014B1 (1 mg)
Batch No. L040/1/014B1 (1 mg)

| | Initial | 40 degree C./75% RH (15 days) |
|---|---|---|
| Assay | 94 | 94.16 |
| Moisture content | 3.54 | 3.43 |
| Dissolution (0.1N HCl; 100 rpm; 900 mL; Paddle at 15 min.) | 93 | 92 |

Pharmacokinetic Analysis in Dogs of Novel Lyophilized Formulation Comprising Arsenic and Comparison with Reference Arsenic Trioxide The purpose of these studies was to determine the oral bioavailability and systemic exposure in dogs of a novel formulation comprising arsenic utilizing lyophilization technology. Dog is a well-documented non-rodent species used routinely to estimate the pharmacokinetic properties of novel agents and formulations in humans.

Study Design

Groups of male dogs (n=3) were administered I.V. formulation of arsenic trioxide (ARSENOX®) at 0.3 mg/kg, unformulated $As_2O_3$ (SV100) at a dose of 2 mg/dog orally or lyophilized formulation of $As_2O_3$ (SV101) at a dose of 2 mg/dog, orally. A fourth group of dogs were administered SV101 at 2 mg/dog orally for confirmatory analysis at a later date. Blood samples were obtained pre-dose and at 0.083, 0.25, 0.5, 1, 2, 4, 6, 8 and 24 h post-dose from the animals in Group 1, and pre-dose and at 0.25, 0.5, 1, 2, 4, 6, 8 and 24 h post-dose from the animals in Groups 2, 3 and 4. Blood samples were immediately placed on wet ice and processed to plasma within 30 minutes of collection. Plasma samples were analyzed at QPS Netherlands BV for arsenic levels using an ICP-MS method with a lower limit of quantification (LLOQ) of 2.50 ng/mL. Individual concentration-time data were used in the calculation of PK parameters of arsenic using WinNonlin™ version 5.2.1.

Results

Following IV bolus dosing of ARSENOX®, plasma levels of arsenic reached 146 ng/ml at Tmax of 1.3 h and declined with a half-life ($t_{1/2}$) of 10.0 h (FIG. 1). Mean systemic clearance was 226 mL/h/kg, and mean Vss was 2734 mL/kg. Following oral administration, SV100 demonstrated very limited absorption with an oral bioavailability ($F^b$ %) of <10%. The oral absorption of SV101 (group 3) is nearly identical to ARSENOX® (I.V.) with Cmax of 182±34.5 ng/ml (vs 146±17.6 ng/ml for ARSENOX®) and AUC0-last (h·ng/mL) of 1416±345 (vs 1115±127 for ARSENOX®) indicating complete oral absorption. These data were confirmed by the repeat administration of SV101 (group 4) which produced nearly identical PK exposure parameters. No tolerability issues were identified during oral administration of $As_2O_3$.

CONCLUSION

Animals were dosed with $As_2O_3$ as intravenous or oral formulation by single administration. Study results showed that the absorption rate and drug exposure of arsenic in the SV101-treated groups were dramatically higher than those in the SV100 group. Complete oral absorption of $As_2O_3$ in the SV101 treated groups was demonstrated by nearly identical systemic exposure of arsenic compared to IV administered ARSENOX®.

Figure 2:
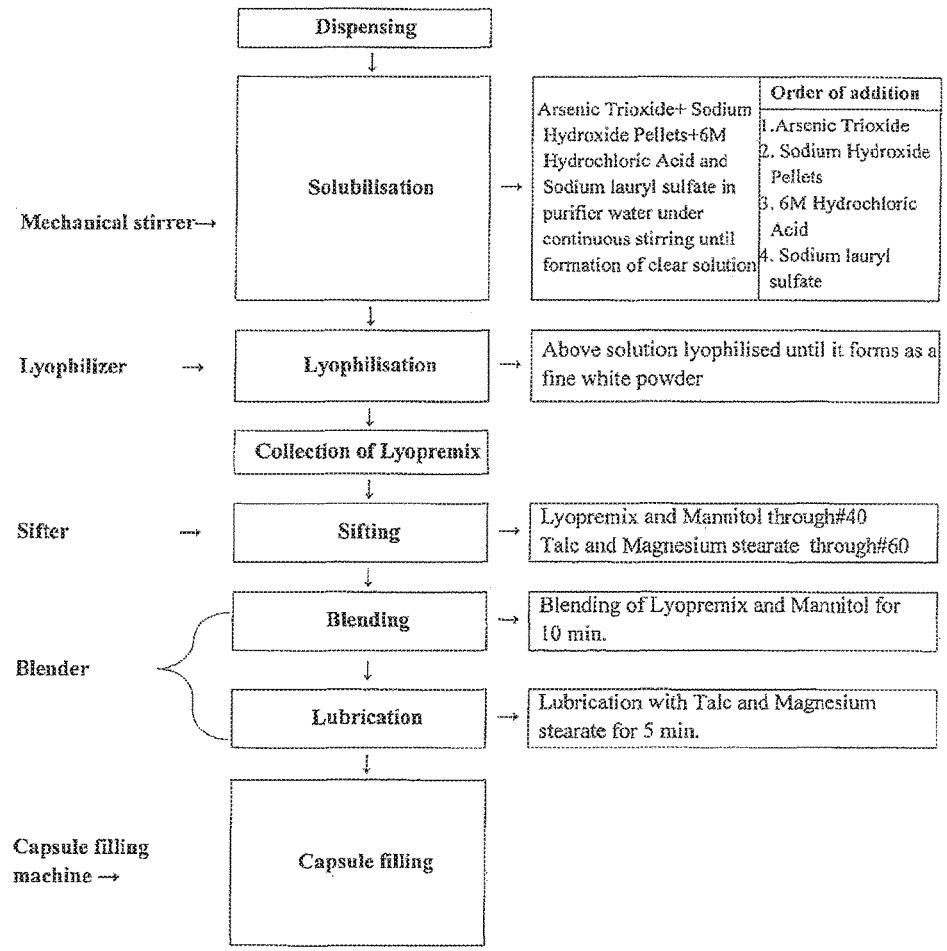
FIG. 2 shows the process flow diagram for lyophilization and capsule making.
Figure 3:
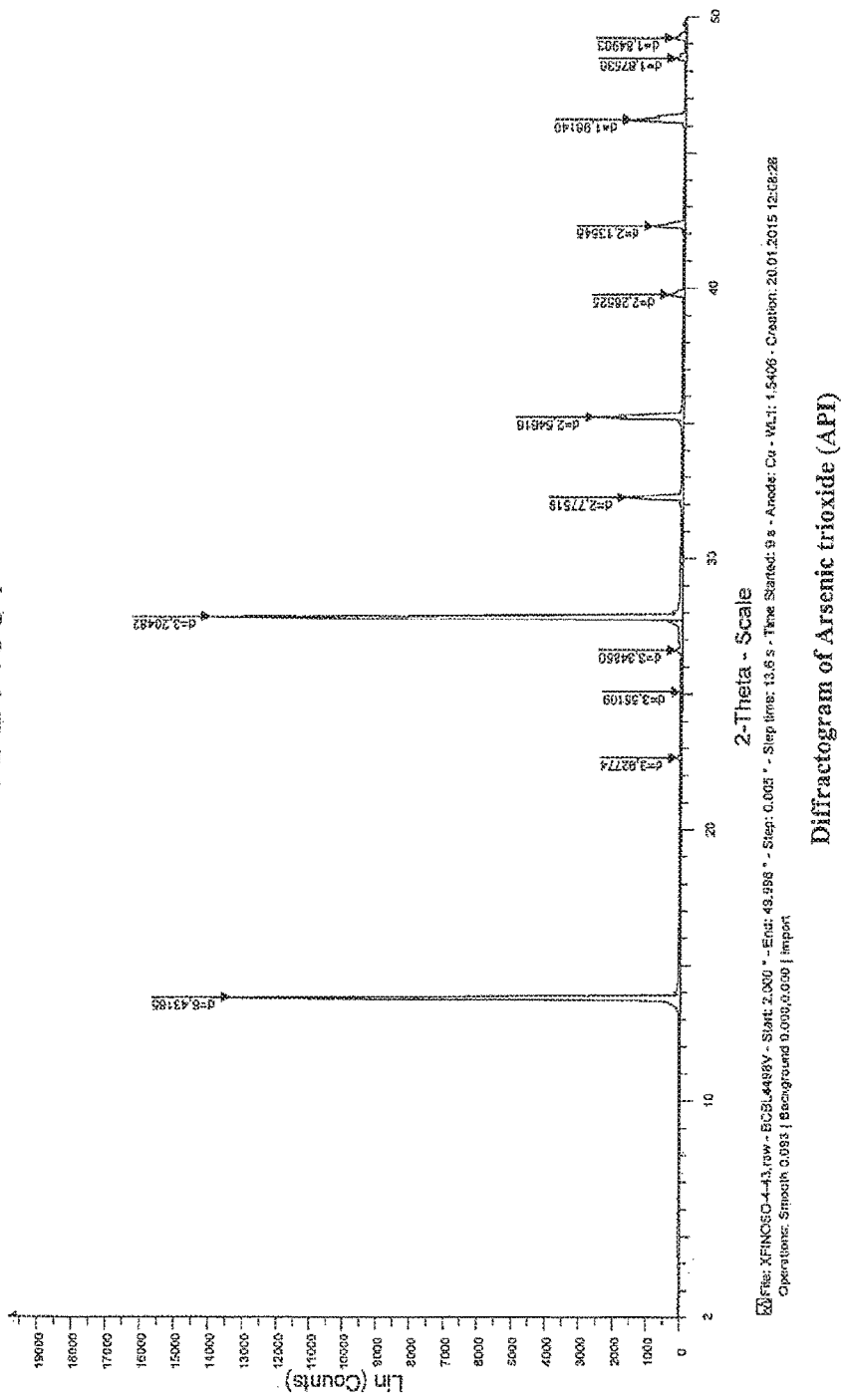
FIG. 3 shows the X-Ray Diffractogram for the arsenic trioxide (API).
Figure 4:
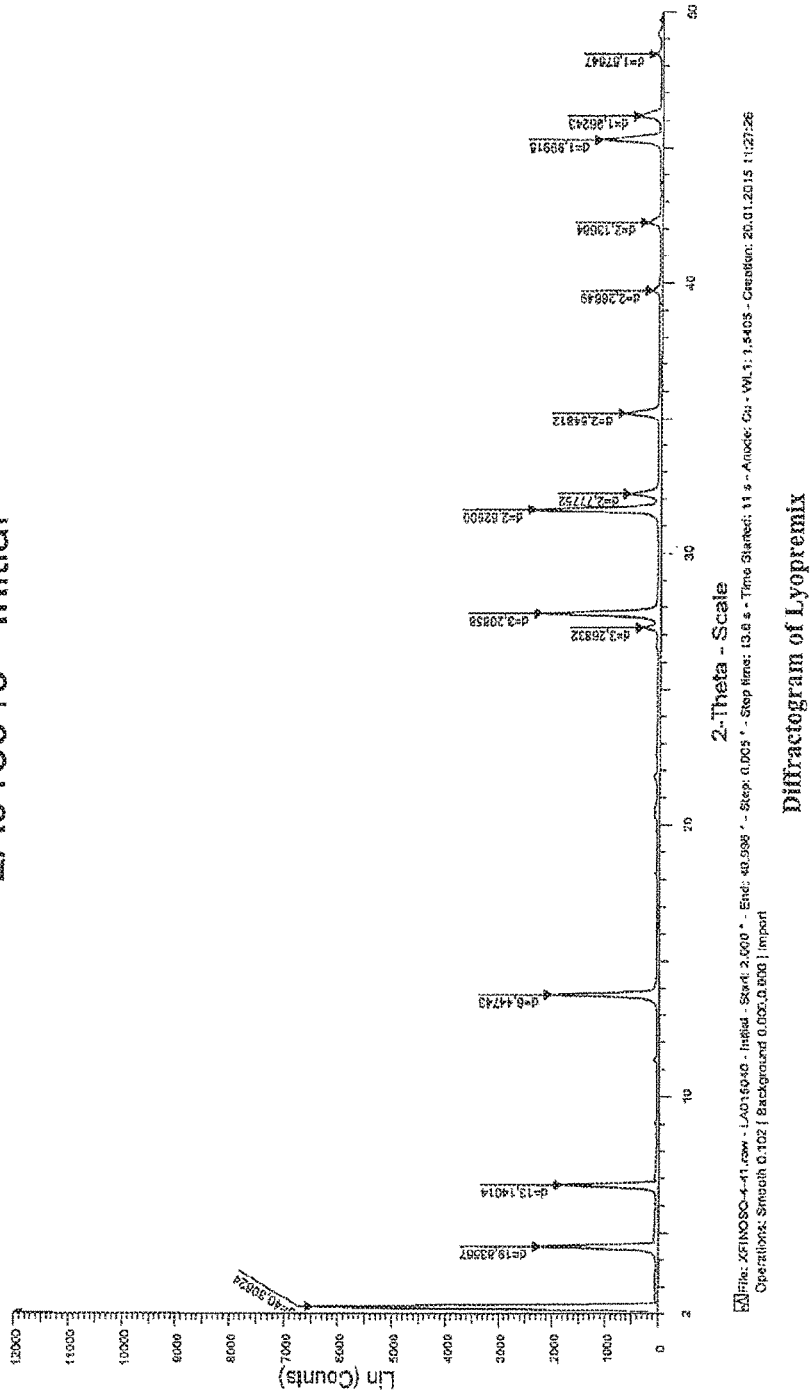
FIG. 4 shows the X-Ray Diffractogram for the Lyopremix of the lyophilized composition comprising arsenic.
Figure 5:
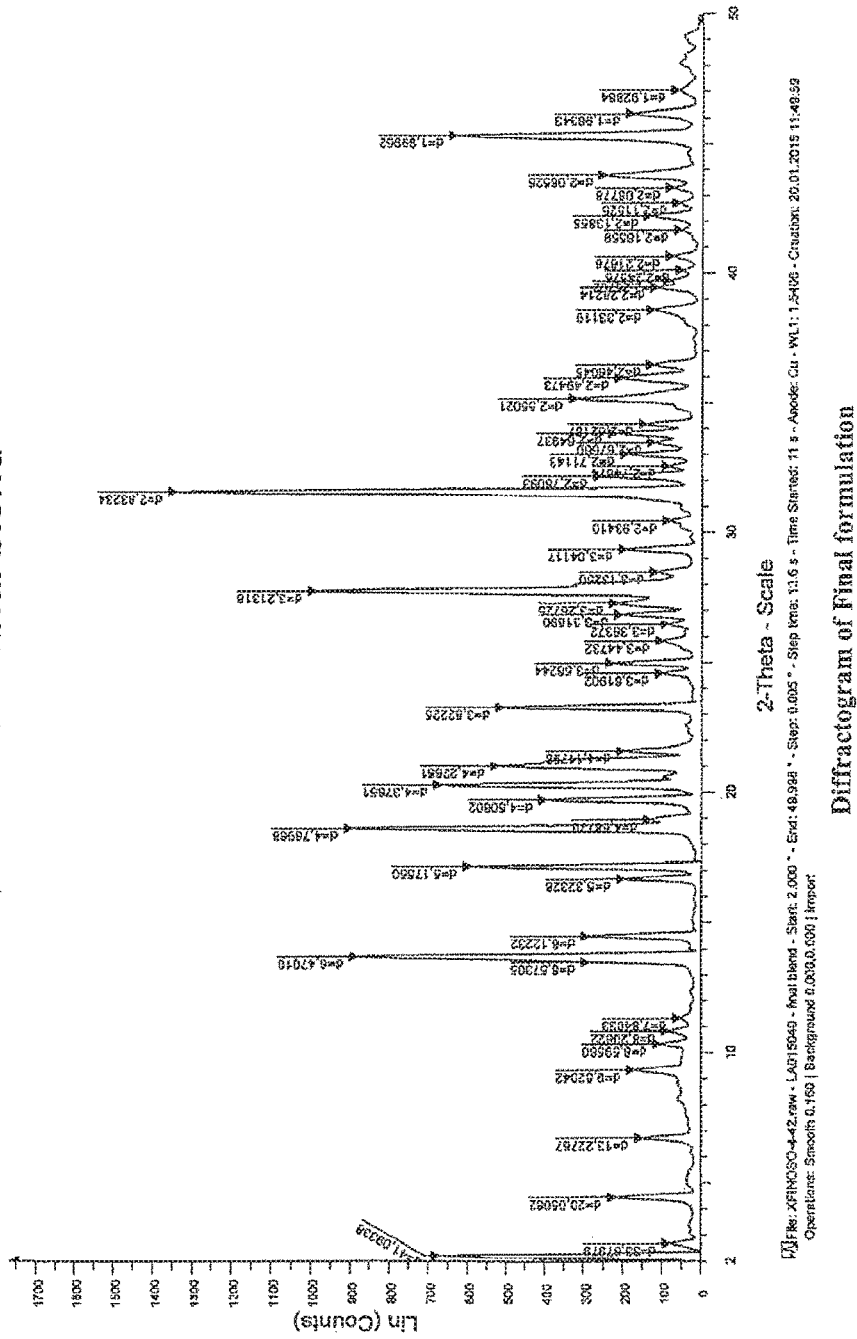
FIG. 5 shows the X-Ray Diffractogram for the Final Blend (pharmaceutical formulation) comprising the lyophilized composition comprising arsenic.
Figure 6:
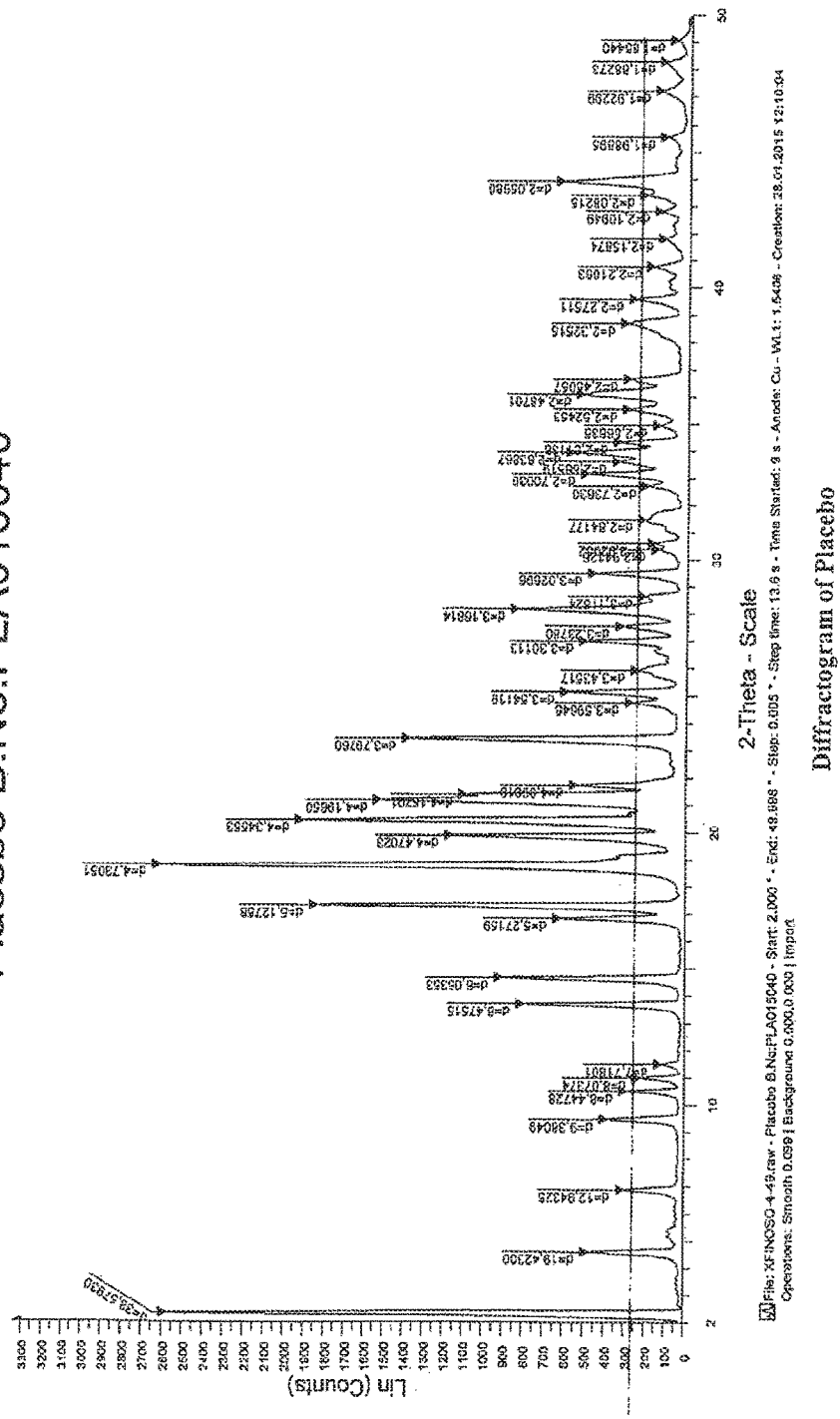
FIG. 6. shows the X-Ray Diffractogram for the placebo.

Characterization of Pharmaceutical Capsules Comprising Lyophilized Composition Comprising Arsenic The objective of these experiments was to characterize the capsule formulation comprising arsenic and summarize their physicochemical properties. The capsule sizes prepared were 1 mg, 2 mg, 5 mg, 10 mg, and 20 mg of the lyopremix formulation comprising arsenic. Four thousand capsules were prepared. The manufacturing process comprised of (A) Lyophilization, and (B) Blending and Lubrication steps. FIG. 2 shows the process flow diagram for capsule making.

(A) Lyophilization

Lyophilization was performed in three stages as follows.

1. Freezing

After solubilization the clear solution was charged into a lyophilizer with set temperature of −40° C. to freeze the product.

TABLE 32

Freezing Step in Lyophilization

| Stage | Temperature (° C.) | Time (min) | Vacuum (millitorrs) |
|---|---|---|---|
| Freezing | −40 | 60 | none |
| Freezing | −40 | 300 | none |
| Extra Freeze (° C.) | −40 | 5 | none |

2. Primary Drying

This stage is also called the "sublimation" stage. In this stage, drying was carried out in presence of vacuum and with increased temperature gradually up to the material converted into solid form. Process parameters followed for this stage are tabulated below.

TABLE 33

Primary Drying

| Ramp | | | Hold | | |
|---|---|---|---|---|---|
| Temperature (° C.) | Time (min) | Vacuum (millitorrs) | Temperature (° C.) | Time (min) | Vacuum (millitorrs) |
| −30 | 60 | 800 | −30 | 60 | 800 |
| −20 | 60 | 500 | −20 | 120 | 500 |
| −5 | 300 | 500 | −5 | 120 | 500 |
| 10 | 120 | 500 | 10 | 60 | 500 |
| 25 | 60 | 500 | 25 | 180 | 500 |

3. Secondary Drying

The material after primary drying was again dried with optimized vacuum and temperature to remove the bound water.

TABLE 34

Secondary Drying

| Temperature (° C.) | Time (min) | Vacuum (millitorrs) |
|---|---|---|
| 25 | 120 | 500 |

(B) Blending and Lubrication

The assay of the Lyopremix was estimated and the actual quantity of the Lyopremix required per capsule was calculated as given below.

Actual quantity of Lyopremix per capsule, in mg,
(A)=[(Quantity per Capsule)×100]/[Assay]
Quantity of Mannitol to be dispersed per capsule in mg, (B)=Theoretical Quantity of Mannitol−[A−Theoretical Quantity of Lyopremix]
Quantity of Mannitol to be dispersed per Batch=B×Batch size The extra quantity of Lyopremix taken based on the actual assay was compensated with Mannitol as shown above. Lyopremix and Mannitol were passed through an ASTM #40 mesh screen and blended for ten minutes, manually, in a polyethylene bag. This blend was lubricated using magnesium stearate and talc, which were pre-sifted through an ASTM #60 mesh for 5 minutes, manually, in a polyethylene bag. This blend was then filled into capsules according to the details given below.

TABLE 35

Fill Weight and Capsule Size

| Strength | Fill Weight (mg) | Size of Capsule |
|---|---|---|
| 20 mg | 200 | 1 |
| 10 mg | 100 | 3 |
| 5 mg | 50 | 4 |
| 2 mg | 20 | 4 |
| 1 mg | 10 | 4 |

Physico-Chemical Characterization

Drug product was characterized for its physicochemical properties and comparative evaluation with raw material was conducted.

1. Particle Size Analysis

The API and the final formulation were characterized for particle size distribution by a Malvern Mastersizer. Data are given in the table below.

TABLE 36

Particle Size Distribution

| Particle Size Distribution | API (micron) | Lyopremix (micron) | Final Formulation (micron) |
|---|---|---|---|
| D(10) | 3.9 | 0.8 | 1.9 |
| D(50) | 21.3 | 2.0 | 80.4 |
| D(90) | 139 | 4.7 | 210.4 |

A significant reduction in PSD at the Lyopremix stage was evident with the above data which likely helped improve the solubility of the arsenic trioxide in the formulation. Applicants, however, are not wishing to be bound by this theory or for that matter any scientific theory. It should be noted that the PSD of the final formulation also comprises about 75% of other additional excipients.

2. Polymorphism

The final formulation was analyzed for API polymorphic form after processing to evaluate any polymorphic form change from as such API. Even the intermediate stage (Lyopremix) was characterized by XRD diffractograms. From this study it was concluded that there was no form change of API in the formulation and it was found to be stable at intermediate stages of manufacturing. Diffractograms are given in FIGS. 3-6, which established that the same polymorphic form was found to be stable throughout the process and in the final formulations.

3. Images Using Scanning Electron Microscope (SEM):

The three samples, that is plain API, Lyopremix, and the Final Blend, were characterized for particle size and morphology characterization by SEM. The images are given in FIG. 7.

4. FTIR

Characterization of the API, the Lyopremix, and the Final Formulation by FTIR was performed. The spectra of Lyopremix and Final formulation are comparable to the observed spectrum of the API.

5. Solubility Study

According to the literature, arsenic trioxide is slightly soluble in cold water and insoluble in alcohol. So, solubility of the API and Lyopremix were studied in these media to evaluate their behavior and the results are provided below.

TABLE 37

| Solubility Studies | | |
|---|---|---|
| Solvent | API (g/100 g) | Lyopremix (g/100 g) |
| Cold water | 2.25 | 40.31 |
| Alcohol | 1.86 | 41.90 |

The solubility study results indicate that the solubility of the API was improved by approximately 20 times by the Lyophilization process of the present invention.

6. Chemical Characterization of Drug Product of all Strengths

TABLE 38

| | | | | | | | |
|---|---|---|---|---|---|---|---|
| | | Chemical Characterization | | | | | |
| No. | Tests | API | 1 mg | 2 mg | 5 mg | 10 mg | 20 mg |
| 1 | Description* | N/A | Complies | Complies | Complies | Complies | Complies |
| 2 | Identification test | N/A | Complies | Complies | Complies | Complies | Complies |
| 3 | Average wt. of the filled capsules (mg) | N/A | 50.1 | 60.7 | 90.2 | 149.8 | 275.3 |
| 4 | Average wt. of capsule filling (mg) | N/A | 10.4 | 20.6 | 51.3 | 101.2 | 201.7 |
| 5 | Water content by KF, % w/v | 2.4 | 2.5 | 2.4 | 2.6 | 2.3 | 2.4 |
| | Disintegration time (min) | N/A | 5 min | 5 min | 6 minutes | 6 minutes | 5 min |
| 7 | Dissolution by ICP-OES (0.1N HCl, Paddle, 100 rpm, 900 mL at 30 min | 10 | 88 | 86 | 95 | 98 | 98 |
| 8 | Assay by ICP-OES (%) | 97.4 | 96.0 | 95.6 | 97.1 | 98.5 | 98.6 |

*Complies as per the respective specification
N/A—not applicable

7. BET Surface Area Measurement

The surface area of the API and the Lyopremix were measured using the BET method for surface area measurement. The specific surface area of the arsenic trioxide API was measured at 0.05 m$^2$/g. The specific surface area of the lyophilized composition comprising arsenic trioxide, or the Lyopremix, was measured at 2.68 m$^2$/g, which is more than a 50-fold increase in the surface area.

Figure 8:
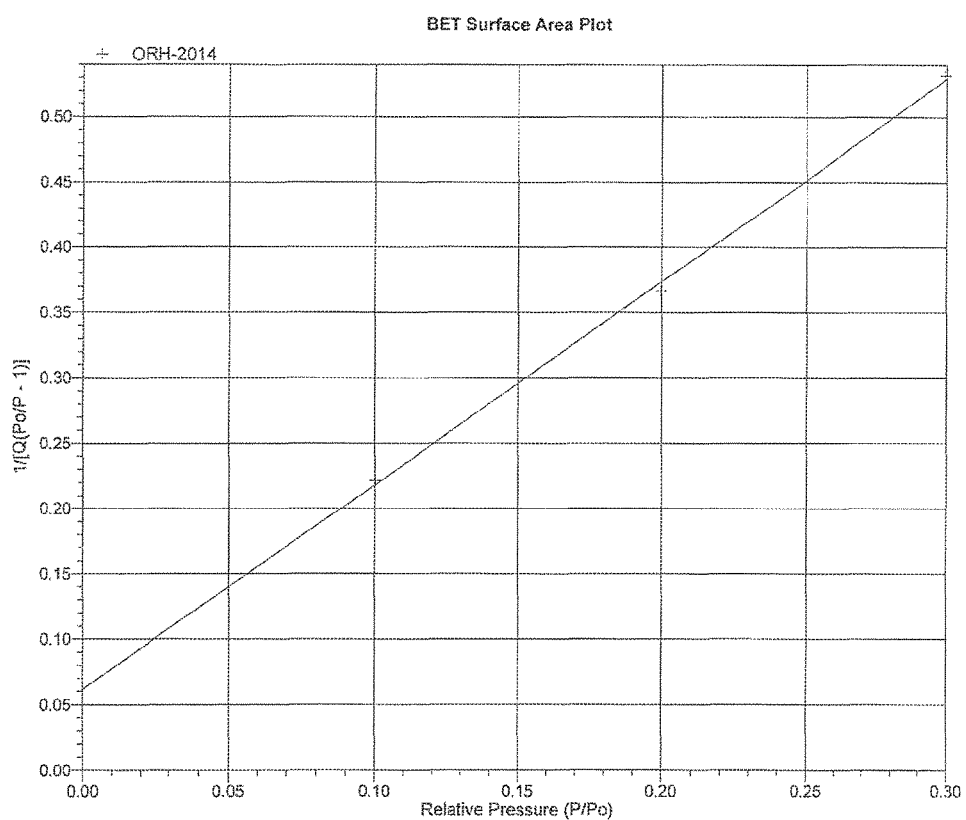
FIG. 8. provides the BET Surface Area Plot for the arsenic trioxide API, which shows how the 1/[Q(Po/P−1)] depends on Relative Pressure P/Po.

Table 39 below provides the surface area data for the API. FIG. 8 provides the BET Surface Area Plot for the API, which shows how the 1/[Q(Po/P−1)] depends on Relative Pressure P/Po.

TABLE 39

| BET Surface Area API | |
|---|---|
| BET Surface Area (API As$_2$O$_3$) | 0.0479 +/− 0.0008 m$^2$/g |
| Slope | 116.430262 +/− 1.959314 g/cm$^3$ |
| Conditions | STP |
| Y Intercept | 1.352003 +/− 0.314575 g/cm$^3$ STP |
| C | 87.116895 |
| Qm | 0.0085 cm$^3$/g STP |
| Correlation Coefficient | 0.9998584 |
| Molecular Cross-Sectional Area | 0.2100 nm$^2$ |

TABLE 39-continued

| | BET Surface Area API | | |
|---|---|---|---|
| No. | Relative Pressure (P/Po) | Quantity Adsorbed ($cm^3$/g STP) | 1/[Q(Po/P-1)] |
| 1. | 0.108368406 | 0.0087 | 14.024907 |
| 2. | 0.154870307 | 0.0095 | 19.275447 |
| 3. | 0.203970489 | 0.0102 | 25.152943 |

Figure 9:
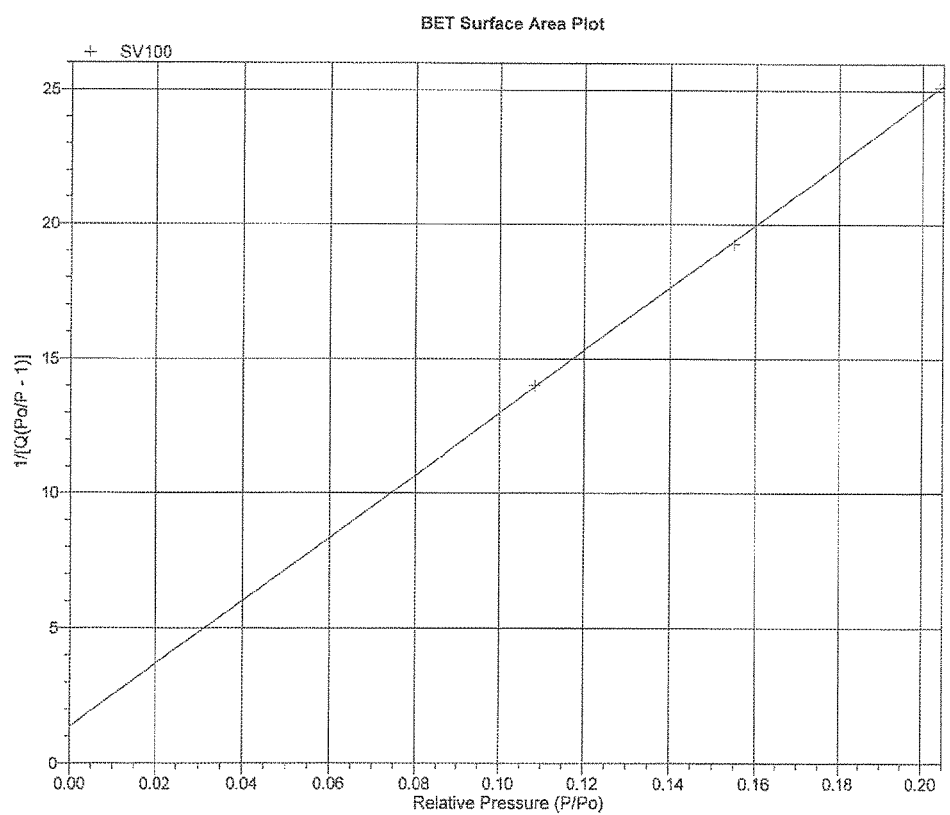
FIG. 9 provides the BET Surface Area Plot for the Lyopremix (lyophilized composition comprising arsenic), which shows how the 1/[Q(Po/P−1)] depends on Relative Pressure P/Po.

Table 40 below provides the surface area data for the Lyopremix. FIG. 9 provides the BET Surface Area Plot for the Lyopremix, which shows how the 1/[Q(Po/P−1)] depends on Relative Pressure P/Po.

TABLE 40

| BET Surface Area Lyopremix | |
|---|---|
| BET Surface Area (Lyopremix) | 2.6838 0 +/− 0.0956 $m^2$/g |
| Slope | 1.560306 +/− 10.056450 g/$cm^3$ |
| Conditions | STP |
| Y Intercept | 0.061695 +/− 0.012176 g/$cm^3$ STP |
| C | 26.290494 |
| Qm | 0.6165 $cm^3$/g STP |
| Correlation Coefficient | 0.9993462 |
| Molecular Cross-Sectional Area | 0.1620 $nm^2$ |

| No. | Relative Pressure (P/Po) | Quantity Adsorbed ($cm^3$/g STP) | 1/[Q(Po/P-1)] |
|---|---|---|---|
| 1. | 0.100287631 | 0.5034 | 0.221423 |
| 2. | 0.199710333 | 0.6803 | 0.366816 |
| 3. | 0.299372148 | 0.8031 | 0.532048 |

Figure 7:
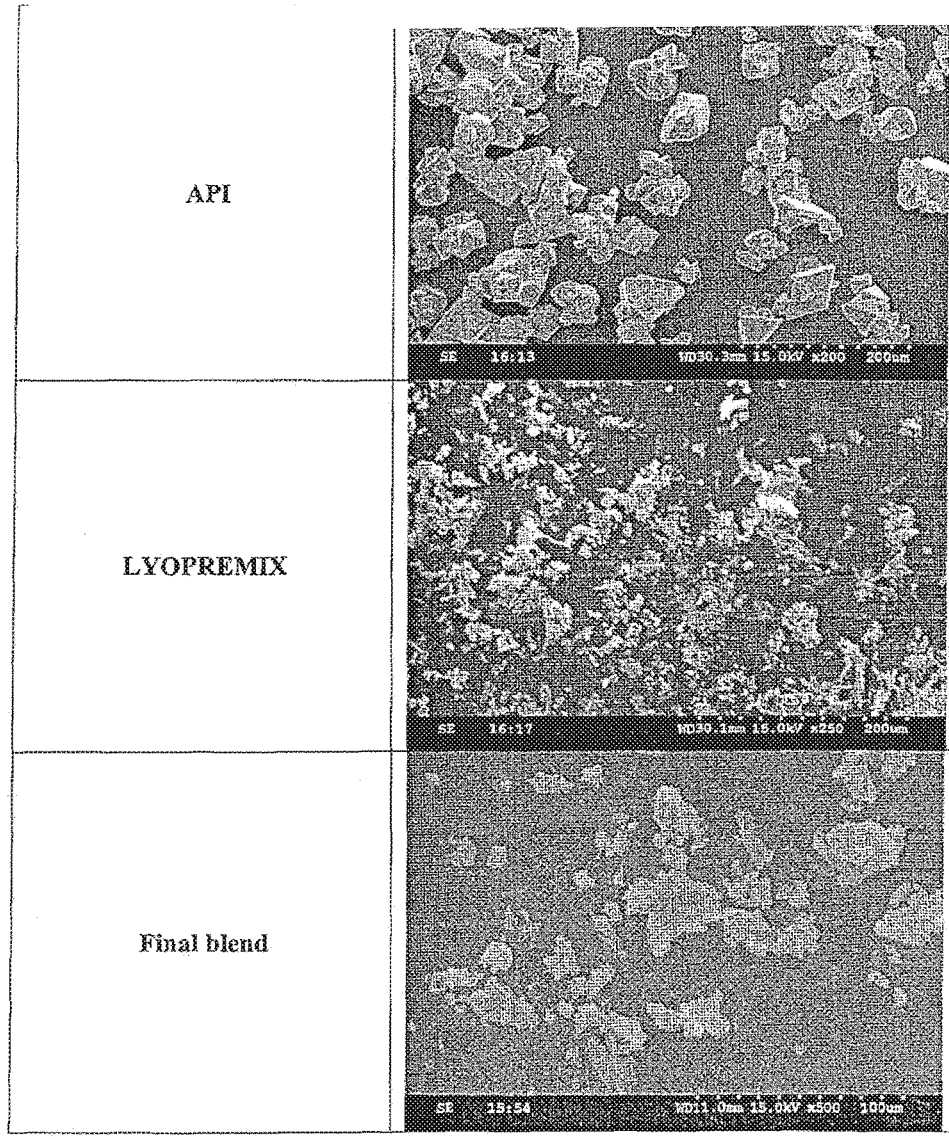
FIG. 7 shows the SEM images of the arsenic trioxide API; the Lyopremix; and the Final Blend.

The polymorphic studies show that the API remained unchanged during the process of manufacturing as well as in the final formulation indicating its stability. SEM images in FIG. 7 show that the API particles size is reduced drastically during lyophilization. The final blend contains other excipients, and thus, its size looks coarser. The chemical properties of the formulation of all the strengths 1, 2, 5, 10, 20 mg capsules were found satisfactory and complying with the finished product specification. Significant improvement in dissolution was observed with the formulation in comparison with API indicating many fold improvement of solubility of arsenic trioxide in the formulation.

What is claimed:

1. A method for preparing a lyophilized composition comprising arsenic (LCCA) comprising:

solubilizing $As_2O_3$ powder and an alkalizing agent in an aqueous medium to form a solution, wherein the alkalizing agent is sodium hydroxide and the amount added is about 10% to about 100% the amount of the $As_2O_3$ powder;

adding a surfactant to the solution; and lyophilizing the solution, wherein the step of lyophilization includes:

freezing the solution to form a frozen $As_2O_3$ product; and drying the frozen product to form particles of an LCCA.

2. The method of claim 1, wherein the alkalizing agent is sodium hydroxide and is added at 100% by weight of the amount of $As_2O_3$ powder.

3. The method of claim 1, wherein the surfactant comprises at least one of sodium lauryl sulfate, polyoxyethylene sorbitan monooleate, betacyclodextrin, poloxamer, tocopheryl polyethylene glycol succinate (TPGS).

4. The method of claim 1, wherein the surfactant is added in amount by weight to the amount by weight of the $As_2O_3$ powder in the range from about 1:10 to about 1:2.

5. The method of claim 1, wherein the surfactant is sodium lauryl sulfate and is added in an amount by weight relative to the $As_2O_3$ powder of about 1:2.

6. The method of claim 1, wherein the freezing step comprises freezing the solution at a temperature in the range of from about −50° C. to about 0° C.

7. The method of claim 1, wherein the solution is frozen for at least about 6 hours.

8. The method of claim 1, wherein the solution is frozen for a time period from about 6 hours to about 8 hours.

9. The method of claim 1, wherein the freezing step comprises a freezing sub step of steadily decreasing the temperature for a time frame of about 60 minutes to about 120 minutes to a freezing temperature of −50° C.

10. The method of claim 1, wherein the solution is frozen at about −50° C. for about 6 hours.

11. The method of claim 1, wherein the drying step comprises a primary drying step and a secondary drying step.

12. The method of claim 11, wherein the primary drying step includes a heating step.

13. The method of claim 12, wherein the heating step comprises heating the frozen product under vacuum from a freezing temperature of about −50° C. to about −30° C. in a time frame of about 30 minutes to about 60 minutes.

14. The method of claim 12, wherein the primary drying step includes drying the frozen product under vacuum at about −30° C.

15. The method of claim 11, wherein the secondary drying step includes a heating step comprising heating the frozen product under vacuum from about −30° C. to about 25° C. in a time frame of about 60 minutes to about 120 minutes.

16. The method of claim 11, wherein the secondary drying step includes drying the LCCA particles under vacuum for about 300 minutes to about 600 minutes.

17. The method of claim 1, wherein the $As_2O_3$ powder has an average particle size, and wherein the LCCA particles have an average particle size that is from about 10 times to about 50 times smaller than the $As_2O_3$ powder average particle size.

18. The method of claim 1, wherein the LCCA particles have a D(90) size range of from about 2 micron to 10 micron.

19. The method of claim 1, wherein the $As_2O_3$ powder has an average BET surface area, and wherein the LCCA particles have an average BET surface area that is from about 2 times to about 80 times greater than the $As_2O_3$ powder average BET surface area.

20. The method of claim 1, wherein the LCCA particles have a BET surface area in the range of from about 0.5 m$^2$/g to 5 m$^2$/g.

21. The method of claim 1, wherein the $As_2O_3$ powder has a solubility in cold water or alcohol, and wherein the solubility of the LCCA particles in cold water or alcohol is about 2 times to about 30 times higher than the solubility of the $As_2O_3$ powder.

22. The method of claim 1, wherein the solubility of the LCCA particles in cold water or alcohol is the range of about 400 mg/ml to about 600 mg/ml.

23. The method of claim 1, wherein the $As_2O_3$ powder has a dissolution rate in water, and wherein the dissolution rate of the LCCA particles in water as measured by ICP-OES is from about 5 times to about 10 times greater than the dissolution rate of the $As_2O_3$ powder.

24. The method of claim 1, wherein the $As_2O_3$ powder has polymorphic form, and wherein the LCCA particles have the same polymorphic form as the $As_2O_3$ powder as measured XRD diffractogram.

25. The method of claim 1, wherein the solution is frozen at about −50° C. for about 4 hours to about 6 hours.

26. The method of claim 1, wherein the solution is frozen at about −50° C. for about 3 hours to about 4 hours.

* * * * *